United States Patent
Hong et al.

(10) Patent No.: US 10,647,694 B2
(45) Date of Patent: May 12, 2020

(54) DIPHENYLAMINOPYRIMIDINE AND TRIAZINE COMPOUND, AND PHARMACEUTICAL COMPOSITION AND USE THEREOF

(71) Applicant: ARROMAX PHARMATECH CO., LTD., Suzhou (CN)

(72) Inventors: Jian Hong, Suzhou (CN); Guobin Liu, Suzhou (CN); Jingbing Wang, Suzhou (CN); Xiaoyong Le, Suzhou (CN)

(73) Assignee: ARROMAX PHARMATECH CO., LTD., Suzhou (CN)

( * ) Notice: Subject to any disclaimer, the term of this patent is extended or adjusted under 35 U.S.C. 154(b) by 0 days.

(21) Appl. No.: 16/307,273

(22) PCT Filed: May 4, 2017

(86) PCT No.: PCT/CN2017/083058
§ 371 (c)(1),
(2) Date: Dec. 5, 2018

(87) PCT Pub. No.: WO2018/018986
PCT Pub. Date: Feb. 1, 2018

(65) Prior Publication Data
US 2019/0256493 A1 Aug. 22, 2019

(30) Foreign Application Priority Data
Jul. 25, 2016 (CN) .......................... 2016 1 0585487

(51) Int. Cl.
| C07D 401/12 | (2006.01) |
| A61P 35/00 | (2006.01) |
| C07D 403/12 | (2006.01) |
| C07D 413/14 | (2006.01) |
| C07D 417/14 | (2006.01) |
| C07D 487/04 | (2006.01) |

(Continued)

(52) U.S. Cl.
CPC .......... *C07D 401/12* (2013.01); *A61K 31/675* (2013.01); *A61P 35/00* (2018.01); *C07D 239/48* (2013.01); *C07D 251/18* (2013.01); *C07D 401/14* (2013.01); *C07D 403/12* (2013.01); *C07D 413/14* (2013.01); *C07D 417/14* (2013.01); *C07D 487/04* (2013.01); *C07D 495/04* (2013.01)

(58) Field of Classification Search
CPC ................................................... C07D 401/12
USPC ...................................................... 514/227.8
See application file for complete search history.

(56) References Cited

U.S. PATENT DOCUMENTS 9,809,572 B2 * 11/2017 Lv .......................... C07D 401/12

FOREIGN PATENT DOCUMENTS

| CN | 101616895 A | 12/2009 |
| CN | 101921236 A | 12/2010 |

(Continued)

*Primary Examiner* — Kahsay Habte
(74) *Attorney, Agent, or Firm* — SZDC Law P.C.

(57) ABSTRACT

A diphenylaminopyrimidine and triazine compound of Formula I, or a pharmaceutically acceptable salt, stereoisomer, hydrate or solvate thereof is disclosed

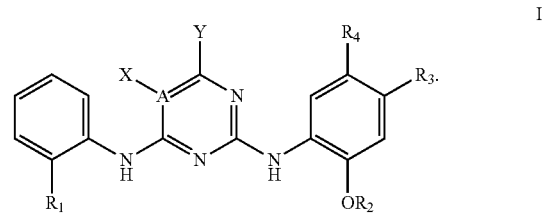

In formula I, A is C or N; X and Y are independently selected from hydrogen, halo, cyano, trifluoromethyl, alkoxy, alkyl, aryl, alkenyl, alkynyl and nitro; or X and Y, together with the atoms to which they are attached, form a phenyl or an heteroaromatic ring; $R_1$ is

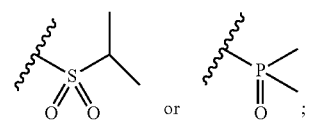

$R_2$ is $CD_3$ or $CD_2CD_3$; $R_3$ is

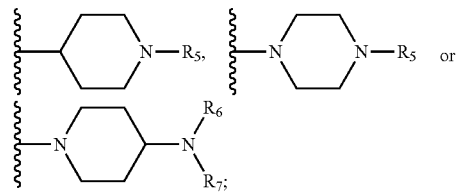

$R_4$ is hydrogen, methyl, trifluoromethyl, cyano or halo; $R_5$ is hydrogen, alkyl, substituted and unsubstituted phenyl, allyl or propargyl; $R_6$ and $R_7$ are independently selected from hydrogen, alkyl, substituted and unsubstituted phenyl, allyl and propargyl; or $R_6$ and $R_7$, together with the nitrogen atom to which they are attached, form a substituted or unsubstituted heterocycloalkyl group. The compound has pharmacodynamic and pharmacokinetic properties and ALK kinase inhibitory activity.

10 Claims, No Drawings

(51) Int. Cl.
*C07D 495/04* (2006.01)
*A61K 31/675* (2006.01)
*C07D 251/18* (2006.01)
*C07D 239/48* (2006.01)
*C07D 401/14* (2006.01)

(56) References Cited

FOREIGN PATENT DOCUMENTS

| | | | |
|---|---|---|---|
| CN | 201280007465 | A | 12/2013 |
| CN | 104109149 | A | 10/2014 |
| CN | 106188138 | A | 12/2015 |
| CN | 201410317076 | A | 2/2016 |
| EP | 2990405 | A1 | 3/2016 |
| WO | 2009143389 | A1 | 11/2009 |
| WO | WO-2014173291 | A1 * | 10/2014 |
| WO | 2015130014 | A1 | 9/2015 |

* cited by examiner

DIPHENYLAMINOPYRIMIDINE AND TRIAZINE COMPOUND, AND PHARMACEUTICAL COMPOSITION AND USE THEREOF

This application is the National State Application of PCT/CN2017/083058, filed on May 4, 2017, which claims priority to Chinese Patent Application No.: CN 201610585487.3, filed on Jul. 25, 2016, which is incorporated by reference for all purposes as if fully set forth herein.

FIELD OF THE INVENTION

The present invention relates to the technical field of biomedicine, and particularly to a diphenylaminopyrimidine and triazine compound, and a pharmaceutical composition and use thereof.

DESCRIPTION OF THE RELATED ART

Anaplastic lymphoma kinase (ALK) is a member of the insulin receptor tyrosine kinase super family. Currently more than twenty ALK fusion proteins arisen from different chromosomal rearrangements have been found, which are involved in the development of anaplastic large cell lymphoma, diffuse large B-cell lymphoma, inflammatory myofibroblastic tumor, neuroblastoma, and the like. ALK fusion proteins play a fundamental role in the development of approximately 5-10% of non-small cell lung cancers. Mutation and over-expression of ALK fusion proteins are associated with a variety of diseases, and the ALK fusion proteins are involved in complex signal transduction, which in turn affects the cell proliferation, differentiation and apoptosis. ALK kinase inhibitors can be used to treat cancers and autoimmune diseases.

In August 2011, Pfizer's selective ALK/c-Met dual inhibitor Crizotinib (trade name Xalkori) was approved by FDA for treating non-small cell lung cancer. Crizotinib and related compounds are disclosed in International Patent Application NO. WO2006021881A2. Crizotinib suffers from the problem of drug resistance in clinical applications, which promotes the development of second-generation ALK kinase inhibitors for the treatment of non-small cell lung cancer and other diseases.

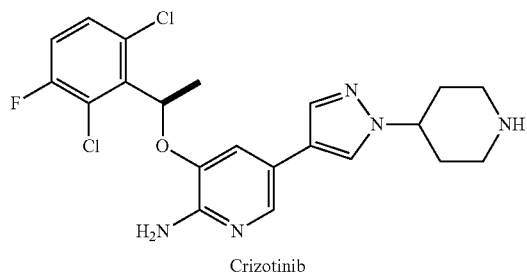 [SMILES: C[C@@H](Oc1cc(-c2cnn(C3CCNCC3)c2)cnc1N)c1c(Cl)ccc(F)c1Cl]

Crizotinib

The second-generation ALK kinase inhibitor drugs are selective ALK kinase inhibitors for treating cancers, cell proliferative disorders and other related diseases. Ceritinib and Alectinib have now been approved for the treatment of patients with ALK-specific non-small cell lung cancer who are resistant to Crizotinib. In addition, studies on the use of ALK selective inhibitors in the treatment of leukemia and lymphoma are also carried out. A Ceritinib-related diphenylaminopyrimidine compound is disclosed in WO2004080980A1 and WO2008073687A2, and an Alectinib-related compound is disclosed in WO2010143664A1.

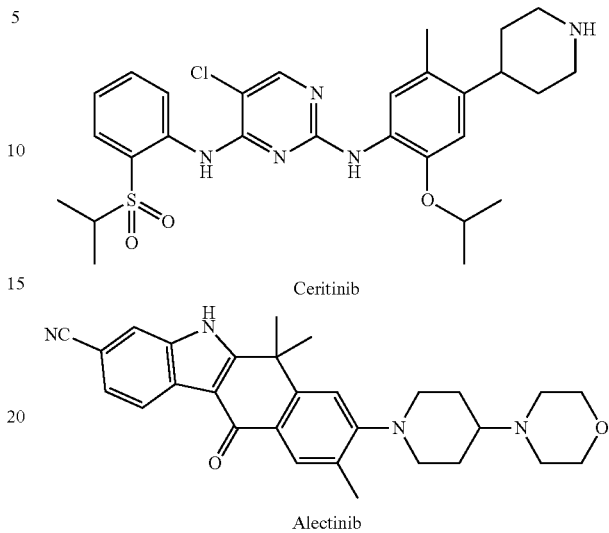

Ceritinib

Alectinib

Although the above listed commercially available ALK kinase inhibitors can alleviate the problems of treatment of ALK-specific lung cancer and drug resistance therein to some extent, there are still problems of insufficient activity and efficacy, which result in a large dose of these drugs during use. For example, Crizotinib needs to be used at a dosage of 500 mg/day, and Alectinib and Ceritinib need to be used at a dosage of more than 750-1200 mg/day, and this indicates that these drugs are far from satisfactory in terms of the therapeutic efficacy.

WO2014173291A1 discloses a series of deuterated diaminopyrimidine compounds to improve the efficacy and druggability of Ceritinib. However, the related efficacy and druggability are not significantly improved. For the ALK kinase inhibitors that have been found, in addition to the problem of efficacy to be further improved, there are also many problems such as poor druggability, prominent drug resistance and obvious toxic and side effects. Therefore, it is of great challenge and necessary to develop a new compound having specific inhibitory effect, low dosage, good druggability and anti-drug resistance effect, and low toxicity.

SUMMARY OF THE INVENTION

To solve the above technical problems, the present invention provides a diphenylaminopyrimidine and triazine compound, or a pharmaceutically acceptable salt, stereoisomer, hydrate or solvate thereof, and use and a pharmaceutical composition thereof. The diphenylaminopyrimidine and triazine compound, or a pharmaceutically acceptable salt, stereoisomer, hydrate or solvate thereof has better pharmacodynamic and pharmacokinetic properties, and can effectively inhibit the ALK kinase activity.

For the above purpose, the following technical solutions are adopted in the present invention.

In one aspect, the present invention provides a diphenylaminopyrimidine and triazine compound of Formula I, or a pharmaceutically acceptable salt, stereoisomer, hydrate or solvate thereof:

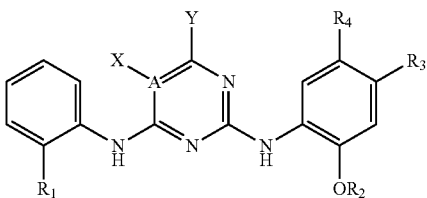

where
A is C or N;

X and Y are independently selected from the group consisting of hydrogen, halo, cyano, trifluoromethyl, alkoxy, alkyl, aryl, alkenyl, alkynyl, and nitro; or X and Y, together with the atoms (C, or C and N) to which they are attached, form a phenyl ring or an heteroaromatic ring, and the heteroaromatic ring contains one or more of oxygen, sulfur and nitrogen heteroatoms;

$R_1$ is

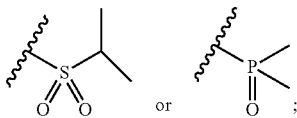

$R_2$ is $CD_3$ or $CD_2CD_3$;
$R_3$ is selected from

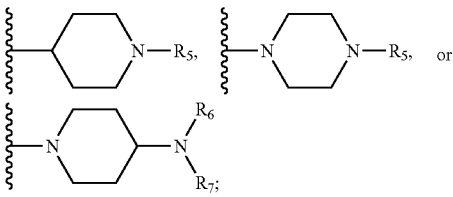

$R_4$ is selected from the group consisting of hydrogen, methyl, trifluoromethyl, cyano and halo;

$R_5$ is selected from the group consisting of hydrogen, alkyl, substituted and unsubstituted phenyl, allyl and propargyl;

$R_6$ and $R_7$ are independently selected from the group consisting of hydrogen, alkyl, substituted and unsubstituted phenyl, allyl and propargyl; or $R_6$ and $R_7$, together with the nitrogen (N) atom to which they are attached, form a substituted or unsubstituted heterocycloalkyl group, and the heterocycloalkyl group contains one or more of oxygen, sulfur, nitrogen, sulfoxide and sulfone groups.

In the present invention, the heteroaromatic ring is preferably acridine, carbazole, cinnoline, quinoxaline, pyrazole, indole, benzotriazole, furan, thiophene, benzothiophene, benzofuran, quinoline, isoquinoline, oxazole, isoxazole, indole, pyrazine, pyridazine, pyridine, pyrimidine, pyrrole or tetrahydroquinoline.

The heterocycloalkyl is preferably oxazolinyl, oxetanyl, pyranyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dihydroazetidinyl, tetrahydrofuranylk, or tetrahydrothienyl.

In the present invention, the alkyl is preferably C1-C10 alkyl, and the alkenyl is preferably C2-C12 alkenyl, more preferably C2-C4 alkenyl, and further preferably ethenyl. The alkynyl is preferably C2-C12 alkynyl, more preferably C2-C4 alkynyl, and further preferably ethynyl.

Preferably, $R_1$ is

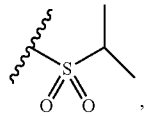 [SMILES: *S(=O)(=O)C(C)C]

$R_2$ is $CD_3$, X is halo, and Y is hydrogen.

More Preferably, the diphenylaminopyrimidine and triazine compound is specifically any one of:

(N4-(2-(isopropylsulfonyl)phenyl)-N2-(2-D3-methoxy-5-methyl-4-(piperidin-4-yl)phenyl)pyrimidin-2,4-diamine);

(5-fluoro-N4-(2-(isopropylsulfonyl)phenyl)-N2-(2-D3-methoxy-5-methyl-4-(piperidin-4-yl)phenyl)pyrimidin-2,4-diamine);

(5-chloro-N4-(2-(isopropylsulfonyl)phenyl)-N2-(2-D3-methoxy-5-methyl-4-(piperidin-4-yl)phenyl)pyrimidin-2,4-diamine);

(5-bromo-N4-(2-(isopropylsulfonyl)phenyl)-N2-(2-D3-methoxy-5-methyl-4-(piperidin-4-yl)phenyl)pyrimidin-2,4-diamine);

(N4-(2-(isopropylsulfonyl)phenyl)-N2-(2-methoxy-5-methyl-4-(piperidin-4-yl)phenyl)-5-(trifluoromethyl)pyrimidin-2,4-diamine);

(2-(isopropylsulfonyl)phenyl)amino)-2-((2-D3-methoxy-5-methyl-4-(piperidin-4-yl)phenyl)amino)pyrimidin-5-nitrile);

(N4-(2-(isopropylsulfonyl)phenyl)-5-methoxy-N2-(2-D3-methoxy-5-methyl-4-(piperidin-4-yl)phenyl)pyrimidin-2,4-diamine);

(N4-(2-(isopropylsulfonyl)phenyl)-N2-(2-D3-methoxy-5-methyl-4-(piperidin-4-yl)phenyl)-5-methylpyrimidin-2,4-diamine);

(5-ethyl-N4-(2-(isopropylsulfonyl)phenyl)-N2-(2-D3-methoxy-5-methyl-4-(piperidin-4-yl)phenyl)pyrimidin-2,4-diamine);

(N4-(2-(isopropylsulfonyl)phenyl)-N2-(2-D3-methoxy-5-methyl-4-(piperidin-4-yl)phenyl)-5-nitropyrimidin-2,4-diamine);

(N4-(2-(isopropylsulfonyl)phenyl)-N2-(2-D3-methoxy-5-methyl-4-(piperidin-4-yl)phenyl)-5-phenylpyrimidin-2,4-diamine);

(N4-(2-(isopropylsulfonyl)phenyl)-N2-(2-D3-methoxy-5-methyl-4-(piperidin-4-yl)phenyl)-5-ethenylpyrimidin-2,4-diamine);

(5-ethynyl-N4-(2-(isopropylsulfonyl)phenyl)-N2-(2-D3-methoxy-5-methyl-4-(piperidin-4-yl)phenyl)pyrimidin-2,4-diamine);

(5-chloro-N2-(2-D6-ethoxy-5-methyl-4-(piperidin-4-yl)phenyl)-N4-(2-(isopropylsulfonyl)phenyl))pyrimidin-2,4-diamine);

(N4-(2-(isopropylsulfonyl)phenyl)-N2-(2-D3-methoxy-4-(4-morpholinopiperidin-1-yl)phenyl)quinazolin-2,4-diamine);

(N4-(2-(isopropylsulfonyl)phenyl)-N2-(2-D3-methoxy-4-(4-methylpiperazin-1-yl)piperidin-1-yl)phenyl)-7H-pyrrolo[2, 3-d]pyrimidin-2,4-diamine);

(N4-(2-(isopropylsulfonyl)phenyl)-N2-(2-D3-methoxy-4-(4-methylpiperazin-1-yl)piperidin-1-yl)phenyl)-5H-pyrrolo[3, 2-d]pyrimidin-2,4-diamine);

N2-(4-(4-(dimethylamino)piperidin-1-yl)-2-D3-methoxyphenyl)-N4-(2-(isopropylsulfonyl)phenyl)thieno[2, 3-d]pyrimidin-2,4-diamine;

(N2-(4-(4-(dimethylamino)piperidin-1-yl)-2-D3-methoxyphenyl)-N4-(2-(iso propylsulfonyl)phenyl)thieno[3, 2-d]pyrimidin-2,4-diamine);

(5-chloro-N4-(2-(isopropylsulfonyl)phenyl)-N2-(2-D3-methoxy-4-(piperazin-1-yl)phenyl)pyrimidin-2,4-diamine);

(5-chloro-N2-(2-D3-methoxy-4-(piperidin-4-yl)phenyl)-N4-(2-(isopropylsul fonyl)phenyl)pyrimidin-2,4-diamine);

(5-chloro-N2-(5-fluoro-2-D3-methoxy-4-(piperidin-4-yl)phenyl)-N4-(2-(iso propylsulfonyl)phenyl)pyrimidin-2,4-diamine);

(5-chloro-N2-(5-chloro-2-D5-ethoxy-4-(piperidin-4-yl)phenyl)-N4-(2-(isopr opylsulfonyl)phenyl)pyrimidin-2,4-diamine);

(5-chloro-N2-(5-chloro-2-D3-methoxy-4-(piperidin-4-yl)phenyl)-N4-(2-(iso propylsulfonyl)phenyl)pyrimidin-2,4-diamine);

(5-chloro-N4-(2-(isopropylsulfonyl)phenyl)-N2-(2-D3-methoxy-4-(piperidin-4-yl)-5-(trifluoromethyl)phenyl)pyrimidin-2,4-diamine);

(5-((5-chloro-4-((2-(isopropylsulfonyl)phenyl)amino)pyrimidin-2-yl)amino)-4-D3-methoxy-2-(piperidin-4-yl)benzonitrile);

(N2-(2-D3-methoxy-4-(piperazin-1-yl)-5-methyl-phenyl)-N4-(2-(isopropyls ulfonyl)phenyl)-1,3,5-triazin-2,4-diamine);

(N2-(2-(isopropylsulfonyl)phenyl)-N4-(2-D3-methoxy-5-methyl-4-(piperidi n-4-yl)phenyl)-1,3,5-triazin-2,4-diamine);

(N2-(2-D3-methoxy-4-(piperazin-1-yl)phenyl)-N4-(2-(iso-propylsulfonyl)phe nyl)-1,3,5-triazin-2,4-diamine);

(5-chloro-N2-(2-D5-ethoxy-4-(piperidin-4-yl)phenyl)-N4-(2-(isopropylsulfo nyl)phenyl)pyrimidin-2,4-diamine);

(N4-(2-(isopropylsulfonyl)phenyl)-N2-(2-D3-methoxy-5-methyl-4-(piperidi n-4-yl)phenyl)quinazolin-2,4-diamine);

(N4-(2-(isopropylsulfonyl)phenyl)-N2-(2-D3-methoxy-5-methyl-4-(piperidi n-4-yl)phenyl)-7H-pyrrolo[2, 3-d]pyrimidin-2,4-diamine);

(N4-(2-(isopropylsulfonyl)phenyl)-N2-(2-D3-methoxy-5-methyl-4-(piperidi n-4-yl)phenyl)-5H-pyrrolo[3, 2-d]pyrimidin-2,4-diamine);

(N4-(2-(isopropylsulfonyl)phenyl)-N2-(2-D3-methoxy-5-methyl-4-(piperidi n-4-yl)phenyl)thieno[2, 3-d]pyrimidin-2,4-diamine);

(5-chloro-N4-(2-(isopropylsulfonyl)phenyl)-N2-(2-D3-methoxy-4-(4-thiomo rpholinopiperidin-1-yl)phenyl)pyrimidin-2,4-diamine);

(N2-(4-(4-amino-[1,4'-bipyridin]-1'-yl)-2-D3-methoxyphenyl)-5-chloro-N4-(2-(isopropylsulfonyl)phenyl)pyrimidin-2,4-diamine);

(5-chloro-N4-(2-(isopropylsulfonyl)phenyl)-N2-(2-D3-methoxy-4-(4-morph olinopiperidin-1-yl)phenyl)pyrimidin-2,4-diamine);

(N2-(2-(isopropylsulfonyl)phenyl)-N4-(2-D3-methoxy-4-(4-(4-methylpipera zin-1-yl)piperidin-1-yl)phenyl)-1,3,5-triazin-2,4-diamine);

(5-chloro-N4-(2-(isopropylsulfonyl)phenyl)-N2-(2-D3-methoxy-4-(4-(4-met hylpiperazin-1-yl)piperidin-1-yl)phenyl)pyrimidin-2,4-diamine);

(2-((5-chloro-2-((4-(4-(dimethylamino)piperidin-1-yl)-2-D3-methoxyphenyl)amino)pyrimidin-4-yl)amino)phenyl)dimethylphosphorus oxide);

(5-chloro-N4-(2-(dimethylphosphoryl)phenyl)-N2-(2-D3-methoxy-5-methyl-4-(piperidin-4-yl)phenyl)pyrimidin-2, 4-diamine);

(N2-(2-(isopropylsulfonyl)phenyl)-N4-(2-D3-methoxy-4-(4-piperidin-4-yl)p henyl)-1,3,5-triazin-2,4-diamine); and (5-chloro-N4-(2-(isopropylsulfonyl)phenyl)-N2-(2-D3-methoxy-4-(piperazin-1-yl)-5-methyl-phenyl)pyrimidin-2,4-diamine).

The structures of the above compounds are respectively as shown below:

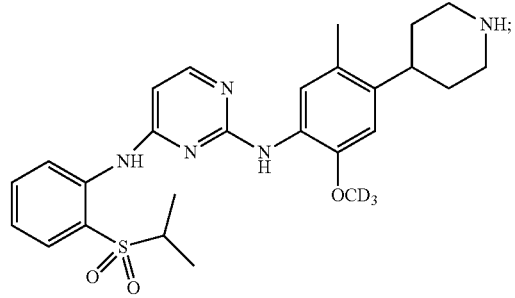

I-1

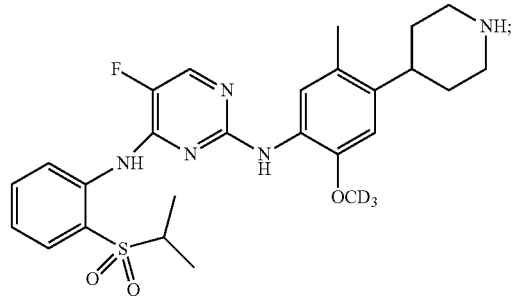

I-2

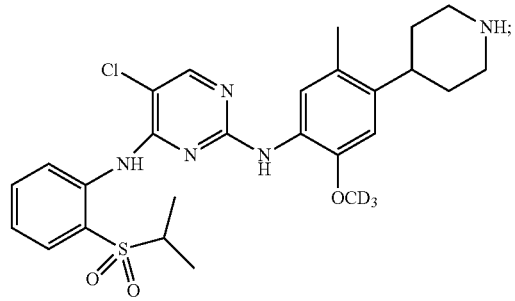

I-3

I-4
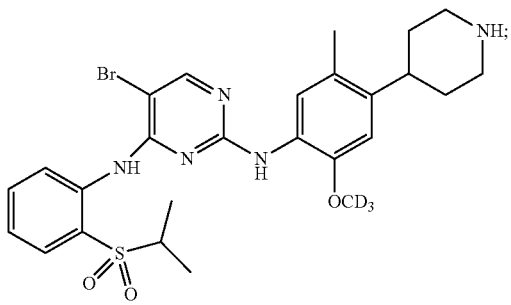
I-5
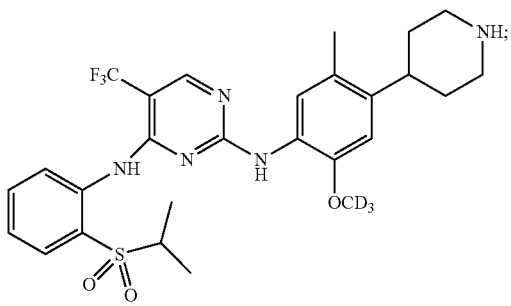
I-6
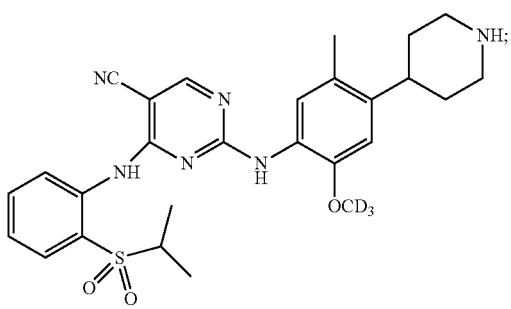
I-7
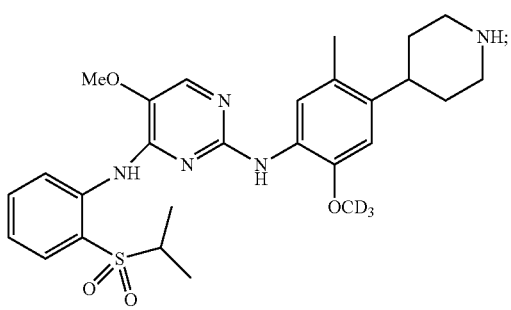
I-8
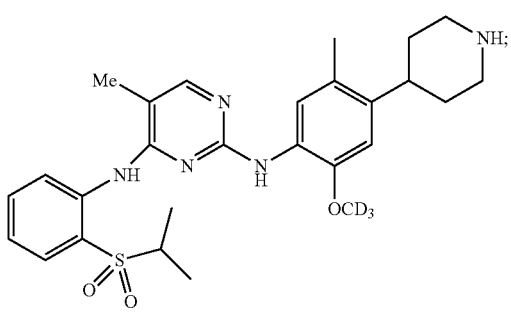
I-9
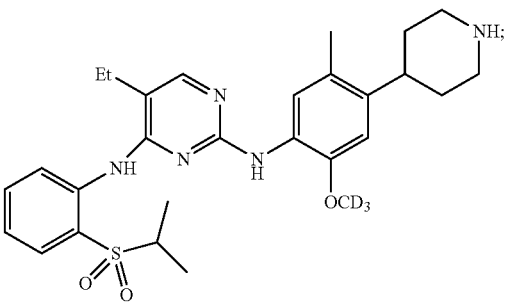
I-10
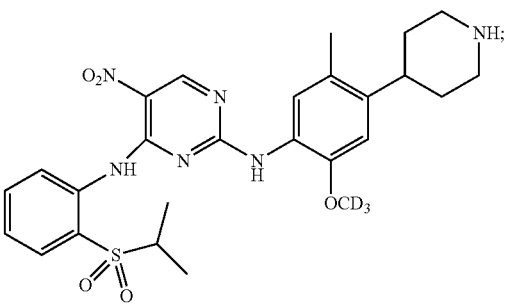
I-11
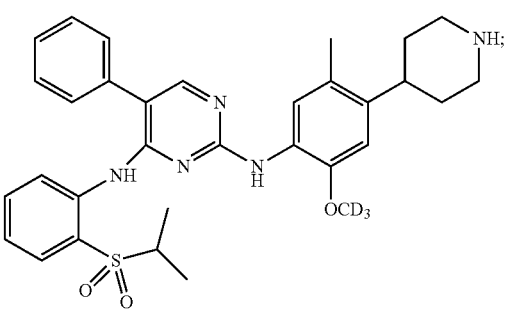
I-12
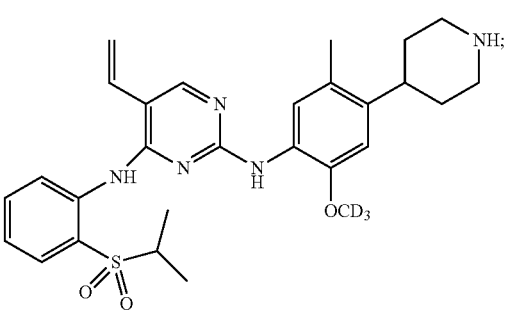
I-13
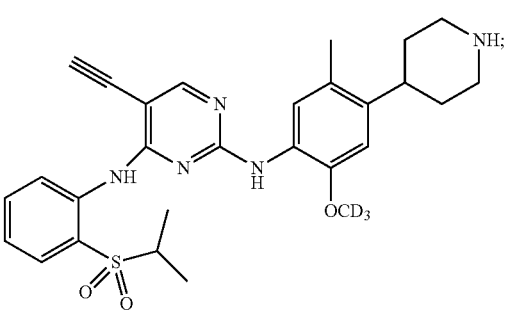

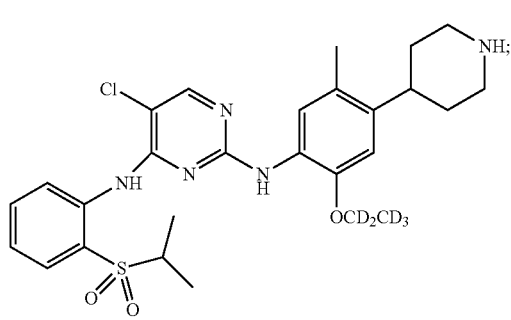
I-14
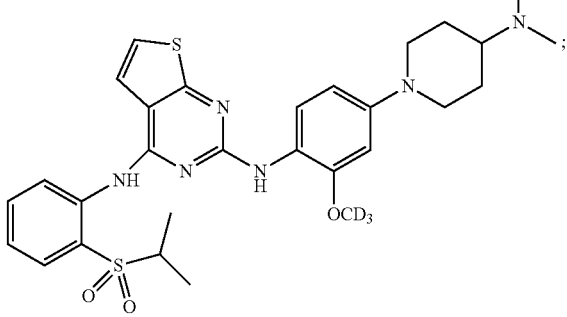
I-18
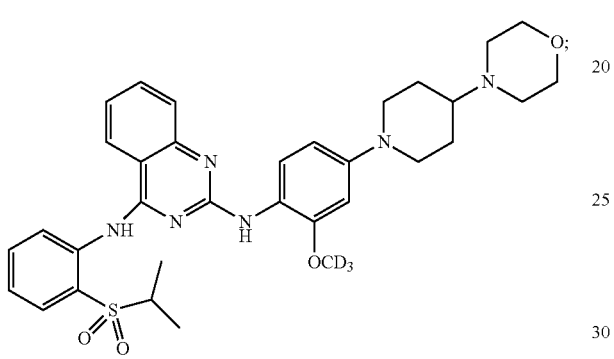
I-15
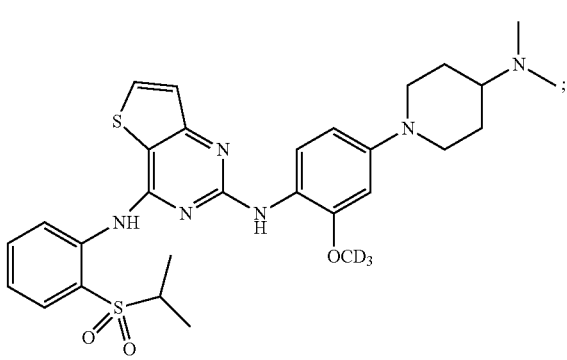
I-19
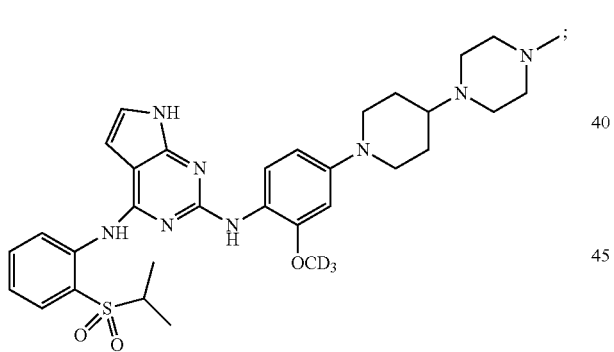
I-16
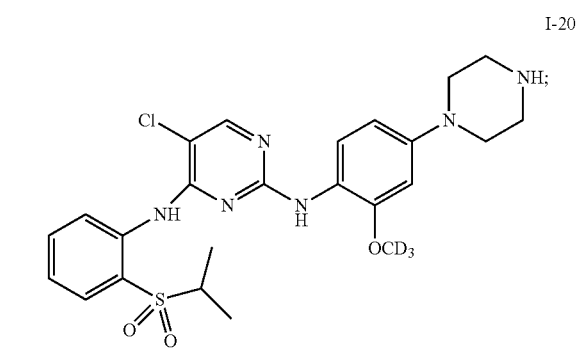
I-20
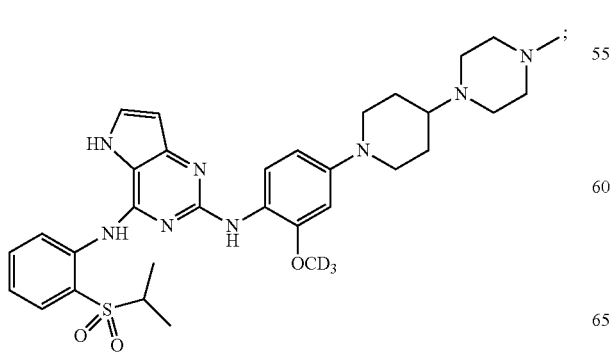
I-17
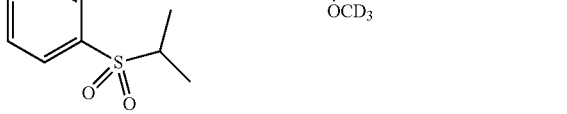
I-21

-continued
I-22
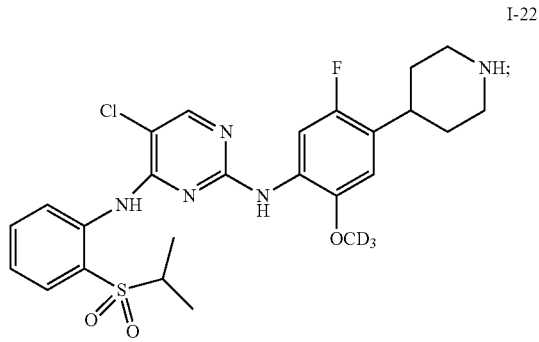
I-23
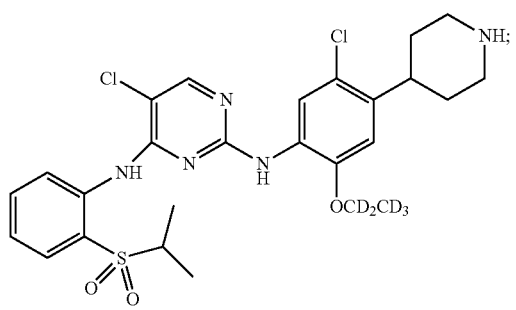
I-24
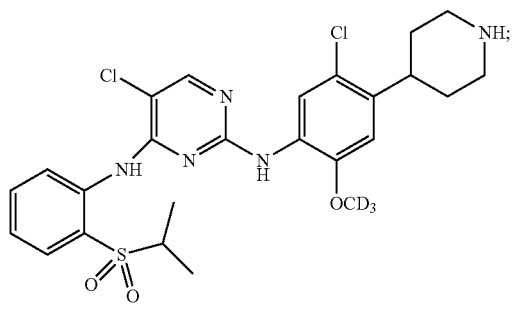
I-25
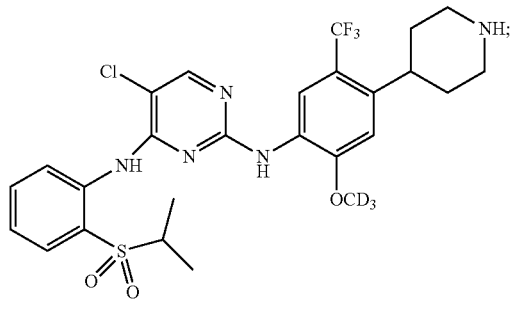
I-26
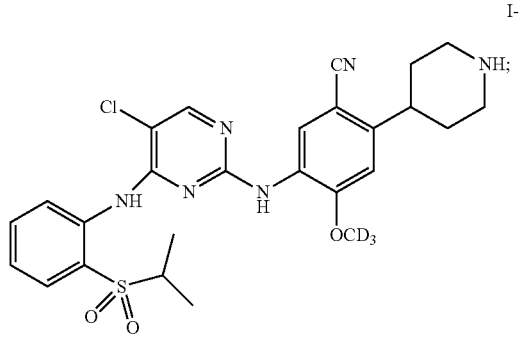
I-27
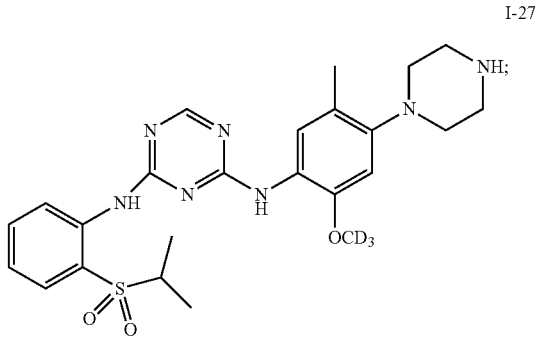
I-28
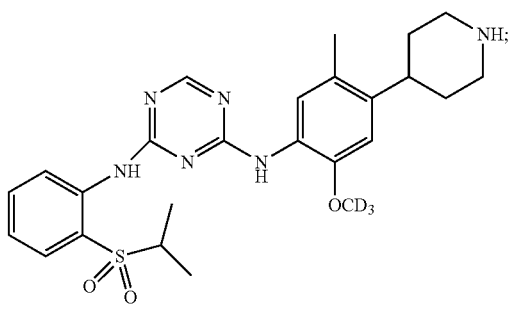
I-29
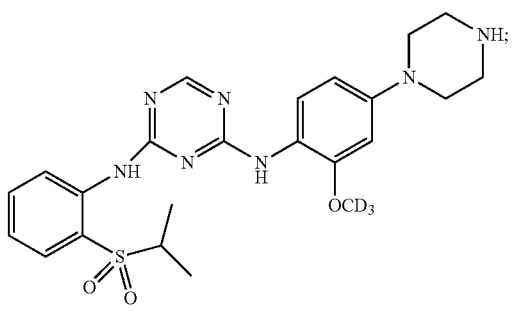
I-30
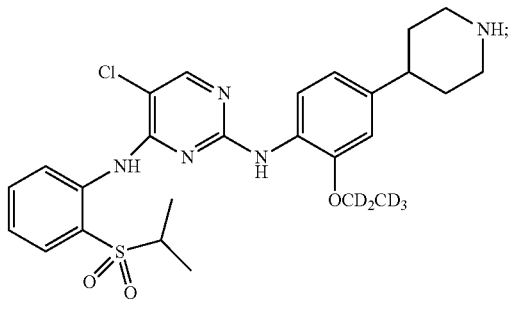
I-31
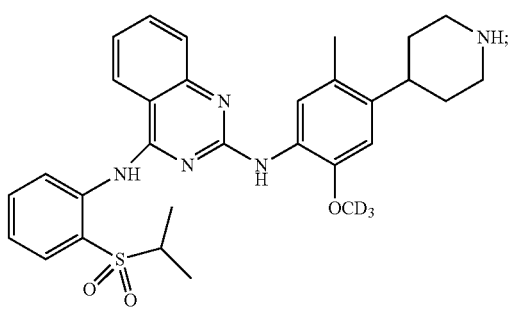

I-32
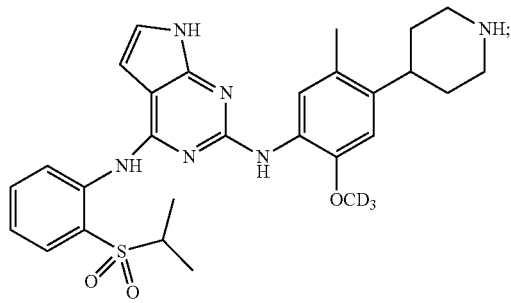
I-33
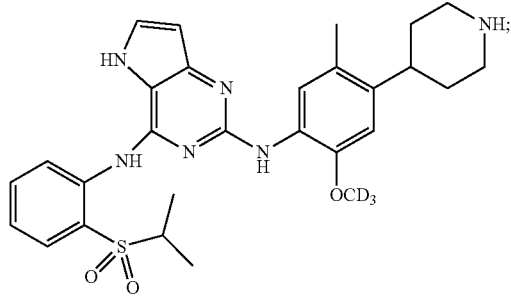
I-34
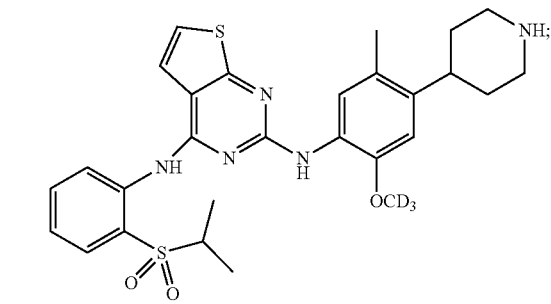
I-35
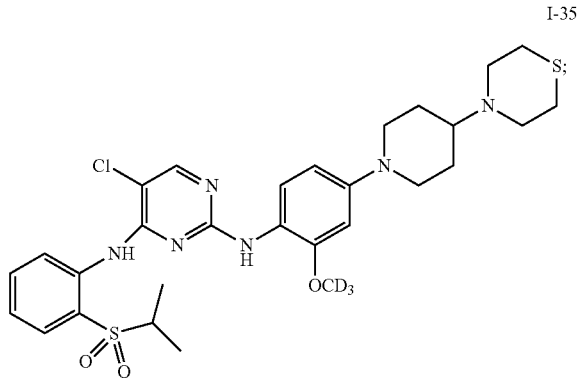
I-36
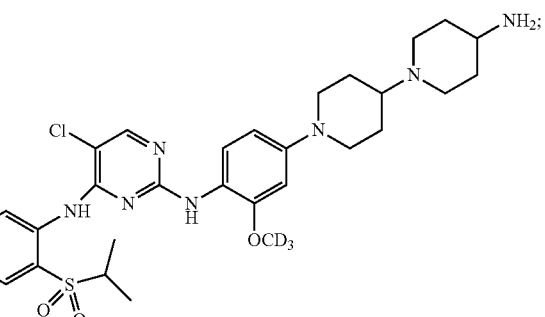
I-37
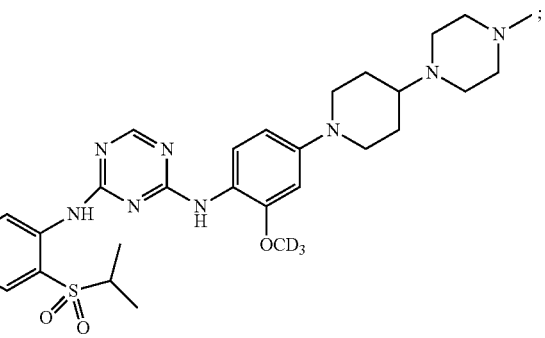
I-38
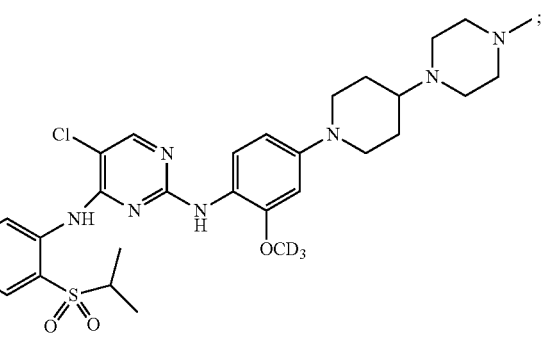
I-39

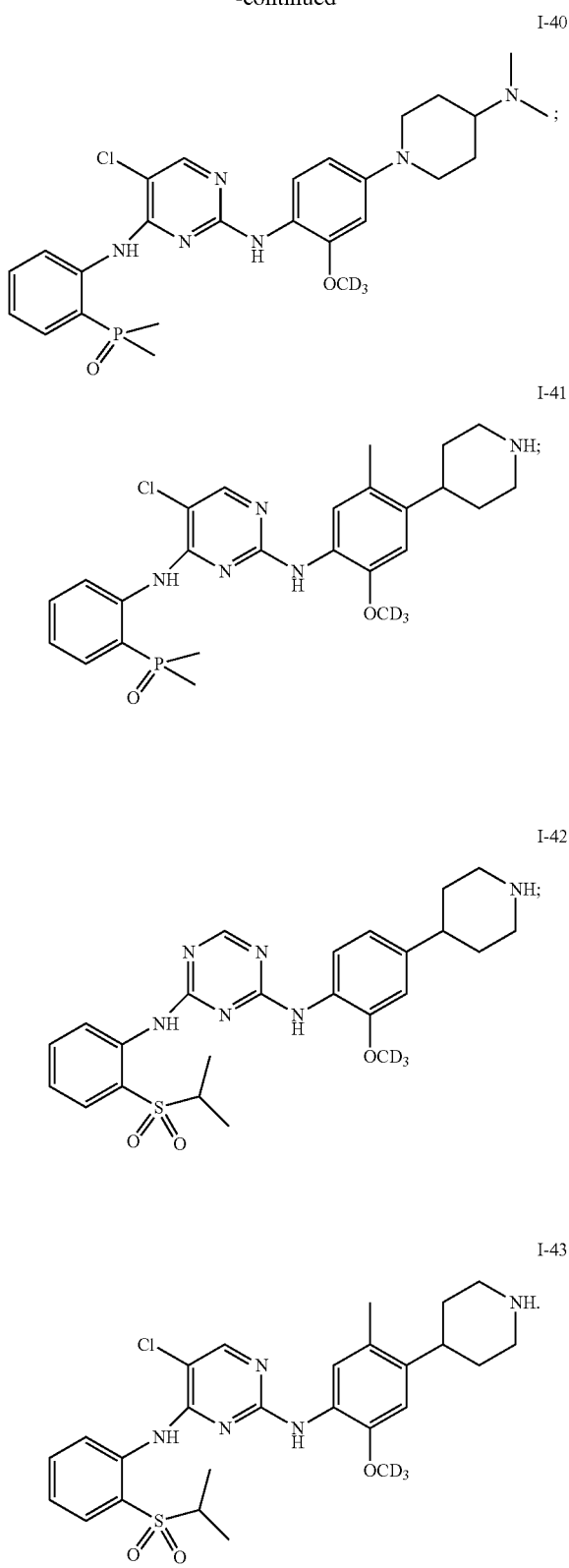

In another aspect, the present invention further provides a method for preparing a diphenylaminopyrimidine and triazine compound of Formula I, comprising the steps of: deprotecting Compound II to obtain a diphenylaminopyrimidine and triazine compound of Formula I, where A, X, Y, $R_1$, $R_2$, $R_3$ and $R_4$ are as defined above. The deprotection and salt formation reactions can be carried out by conventional methods and conditions for such reactions in the art.

In the present invention, the method for preparing a diphenylaminopyrimidine and triazine compound of Formula I further comprises the step of coupling Compound III to Compound IV in the presence of a palladium catalyst, to obtain Compound II, where A, X, Y, $R_1$, $R_2$, $R_3$ and $R_4$ are as defined above. PG is a protecting group, and may be t-butoxycarbonyl (Boc), Carbobenzyloxy (CBz), or trichloroethoxycarbonyl (Troc), and preferably Boc.

In the present invention, the method for preparing a diphenylaminopyrimidine and triazine compound of Formula I further comprises the step of coupling Compound V to Compound VI, to obtain Compound III,

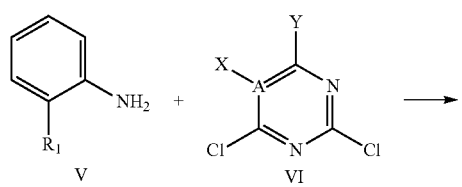

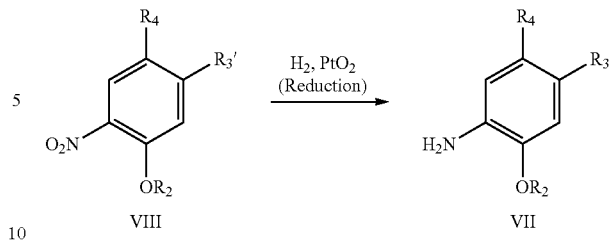

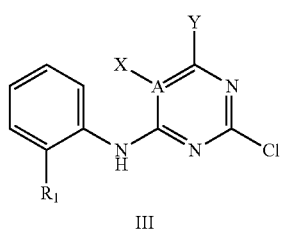

where A, X, Y, $R_1$, $R_2$, $R_3$ and $R_4$ are as defined above. The coupling can be carried out by conventional methods and conditions for such reactions in the art.

In the present invention, where $R_3$ is piperidinyl, the method for preparing a diphenylaminopyrimidine and triazine compound of Formula I further comprises the step of protecting the amino group in group $R_3$ in the Compound VII, to obtain Compound IV,

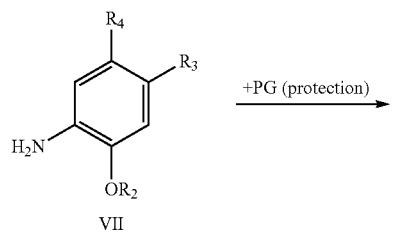

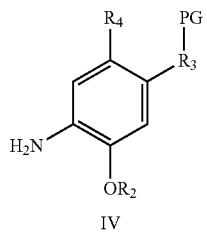

where $R_1$, $R_2$, $R_3$ and $R_4$ are as defined above; and PG is a protecting group, and may be Boc, CBz or Troc, and preferably Boc. The protection reaction can be carried out by conventional methods and conditions for such reactions in the art.

In the present invention, when $R_3$ is piperidinyl, the method for preparing a diphenylaminopyrimidine and triazine compound of Formula I further comprises the step of reducing the nitro group and the pyridinyl group in $R_3'$ in Compound VIII, to obtain Compound VII, where $R_1$, $R_2$, $R_3$, $R_3'$ and $R_4$ are as defined above. The reduction reaction can be carried out by conventional methods and conditions for such reactions in the art.

In the present invention, when $R_3$ is piperidinyl, and $R_3'$ is pyridinyl, the method for preparing a diphenylaminopyrimidine and triazine compound of Formula I further comprises the step of subjecting Compound IX and Compound X to Suzuki coupling reaction, to obtain Compound VIII,

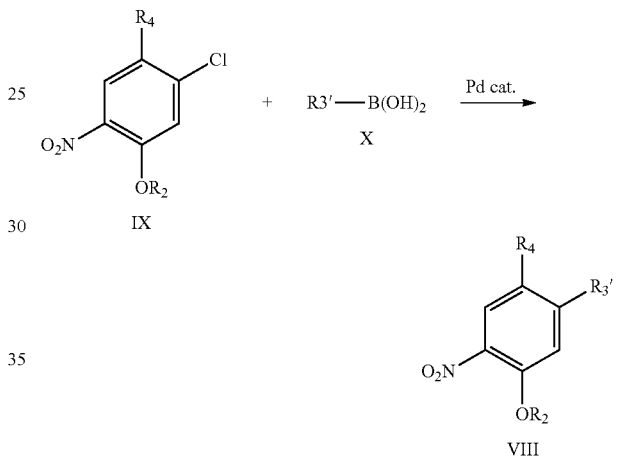

where $R_1$, $R_2$, $R_3'$ and $R_4$ are as defined above. The Suzuki coupling reaction can be carried out by conventional methods and conditions for such reactions in the art.

In the present invention, the method for preparing a diphenylaminopyrimidine and triazine compound of Formula I further comprises the step of performing a substitution reaction on Compound XI, to obtain Compound IX,

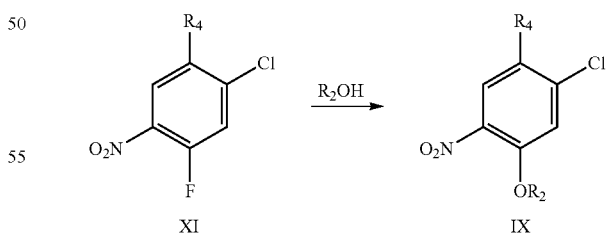

where $R_1$, $R_2$ and $R_4$ are as defined above. The substitution reaction can be carried out by conventional methods and conditions for such reactions in the art.

Furthermore, in the present invention, when $R_3$ is a mono-PG protected piperazinyl group, the method for preparing a diphenylaminopyrimidine and triazine compound of Formula I further comprises the step of reducing the nitro group in Compound VIII, to obtain Compound IV.

By using the synthesis method described in the present invention as well as the synthesis methods known in the art, a diphenylaminopyrimidine and triazine compound of Formula I can be obtained with a high purity and yield, after purification by conventional methods known in the art, such as filtration, recrystallization, chromatography, column chromatography, distillation, and any combinations thereof.

In the present invention, the term "alkyl" is a branched or linear saturated aliphatic hydrocarbyl having specified number of carbon atoms, for example, a group having 1, 2, 3, 4, 5, 6, 7, 8, 9, or 10 carbon atoms in a linear or branched structure, as defined in "C1-C10 alkyl". For example, "C1-C10 alkyl" includes particularly methyl, ethyl, n-propyl, isopropyl, n-butyl, t-butyl, isobutyl, pentyl, hexyl, heptyl, octyl, nonyl, decyl and the like.

In the present invention, the term "alkoxy" represents a group formed by attaching an oxygen atom to an alkyl group, that is, "RO—", in which R is alkyl.

In the present invention, the term "cycloalkyl" refers to a monocyclic or polycyclic group in which the ring members are exclusively carbon, for example, a cycloalkyl group having 1 to 3 rings consisting of preferably 3-20 carbon atoms, and more preferably 3-10 carbon atoms, such as cyclopropyl, cyclobutyl, cyclopentyl, cyclohexyl, cycloheptyl, cyclooctyl, cyclodecyl or cyclododecyl.

In the present invention, the term "heterocycloalkyl", as used herein alone or as part of another group, refers to a 4- to 12-membered monocyclic or polycyclic group having 1 to 4 heteroatoms such as one or more of nitrogen, oxygen and sulfur, in which each ring may contain one or more double bonds, but none of the rings have a fully conjugated it-electron system. Furthermore, any heterocycloalkyl ring may be fused to a cyclalkyl, aryl, heteroaryl or heterocycloalkyl ring. The heterocycloalkyl groups within the scope of this definition include, but are not limited to: oxazolinyl, oxetanyl, pyranyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, dihydroazetidinyl, tetrahydrofuranyl, and tetrahydrothienyl, and an N-oxide thereof. The heterocycloalkyl can be attached to other groups via a carbon atom or a heteroatom therein.

In the present invention, the term "alkenyl" refers to a linear, branched or cyclic non-aromatic hydrocarbyl having specified number of carbon atoms and at least one carbon-carbon double bond. Preferably, there is one carbon-carbon double bond, and up to four non-aromatic carbon-carbon double bonds may be present. Here, "C2-C12 alkenyl" means an alkenyl group having 2 to 12 carbon atoms. "C2-C4" alkenyl means an alkenyl group having 2 to 4 carbon atoms, including ethenyl, propenyl, 2-methyl-propenyl, 1-butenyl, and 2-butenyl. The alkenyl may contain a double bond in the linear, branched or ring portion.

In the present invention, the term "alkynyl" refers to a linear, branched or cyclic hydrocarbon radical containing specified number of carbon atoms and at least one carbon-carbon triple bond. Up to three carbon-carbon triple bonds may be present. Here, "C2-C12 alkynyl" means an alkynyl group having 2 to 12 carbon atoms. "C2-C4 alkynyl" means an alkynyl group having 2 to 4 carbon atoms, including ethynyl, propynyl, 1-butynyl, 2-butynyl, and the like.

In the present invention, the term "aryl" refers to any stable monocyclic or bicyclic carbon ring having up to 7 atoms in which at least one ring is an aromatic ring. Examples of aryl include phenyl, naphthyl, tetrahydronaphthyl, 2,3-dihydroindenyl, biphenyl, phenanthryl, anthryl or acenaphthyl. It will be understood that in the case where the aryl substituent is a bicyclic substituent and one of the rings is a non-aromatic ring, the linkage is performed via the aromatic ring.

In the present invention, the term "heteroaromatic ring" refers to a stable monocyclic or bicyclic ring having up to 7 atoms, where at least one ring is an aromatic ring and contains 1-4 heteroatoms selected from O, N and S. Examples of heteroaromatic ring include, but are not limited to, acridine, carbazole, cinnoline, quinoxaline, pyrazole, indole, benzotriazole, furan, thiophene, benzothiophene, benzofuran, quinoline, isoquinoline, oxazole, isoxazole, indole, pyrazine, pyridazine, pyridine, pyrimidine, pyrrole or tetrahydroquinoline. As defined hereinafter, "heteroaromatic ring" is also understood to include an N-oxide derivative of any nitrogen-containing heteroaryl groups. In the case where the heteroaryl substituent is a bicyclic substituent and one ring is non-aromatic or does not contain a heteroatom, it is to be understood that the linkage is performed via the aromatic ring or via a ring comprising a heteroatom, respectively.

In the present invention, "Cx1-Cy1" alkyl (where x1 and y1 are an integer respectively), cycloalkyl, heterocycloalkyl, aryl, and heteroaryl, having defined number of carbon atoms, such as "C1-12 alkyl", represent a C1-12 alkyl group which does not contain a substituent.

In the present invention, the term "halo" represents fluoro, chloro, bromo or iodo.

In the present invention, the term "cyano" represents

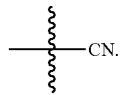

For each variable, any combination of the above groups is also contemplated herein. It will be appreciated that the substituents and substitution patterns on the compounds provided herein can be determined by one of ordinary skill in the art, to provide compounds that are chemically stable and can be synthesized using techniques known in the art and techniques set forth herein.

Any of the diphenylaminopyrimidine and triazine compounds of Formula I can be synthesized using standard synthesis techniques known to those skilled in the art or using synthesis methods known in the art in combination with the synthesis method described herein. Additionally, the solvents, temperatures, and other reaction conditions mentioned herein may vary depending on the techniques in the art. As a further guidance, the following synthesis methods may also be utilized.

In certain embodiments, provided herein are a method for preparing a diphenylaminopyrimidine and triazine compound of Formula I, and a method of using the same. In certain embodiments, the compound described herein can be synthesized through a synthesis scheme below, or the target compound can be synthesized using a method similar to that described below by selecting an appropriate starting material.

The starting material used to synthesize the compound described herein may be synthesized or is commercially available. The compound described herein and other related compounds having different substituents can be synthesized using techniques and starting materials known to those skilled in the art, for example, as described in Paquette, "Encyclopedia of Reagents for Organic Synthesis" (Wiley 2009); March, "Advanced Organic Chemistry", Fourth Edition, (Wiley1992); Carey and Sundberg, "Advanced Organic Chemistry", Fourth Edition, Vol. A and B (Plenum 2000, 2001); Green and Wuts, "Protective Groups in Organic Synthesis", Third Edition, (Wiley1999); Fieser and Fieser, "Reagents for Organic Synthesis", Vol. 1-17 (John Wiley and Sons, 1991); "Organic Reactions", Vol. 1-40 (John Wiley and Sons, 1991), and Larock "Comprehensive Organic Transformations" (VCH Publishers Inc., 1999) (which are all incorporated herein by reference in their entireties). A general method for preparing the compound disclosed herein can be derived from reactions known in the art, which may be carried out with modified reagents and under modified conditions deemed appropriate by those skilled in the art, to synthesize the target compound. The following synthesis methods can be used as a basic guidance.

After each reaction is completed, the reaction product can be processed (separated and purified) using conventional techniques including, but not limited to, filtration, distillation, crystallization, chromatography, and so on. These products can be characterized using conventional analytical methods, including physical constants and profile data (m.p, HPLC, LC-MS, NMR and optical rotation, etc.). The compound described herein can be prepared as a single isomer using the synthesis method described herein.

Pharmaceutical Compositions and Preparations:

In another aspect, the present invention provides a pharmaceutical composition including any compound or a pharmaceutically acceptable salt, stereoisomer, hydrate or solvate thereof of the present invention, and one or more pharmaceutically acceptable carriers or excipients. The pharmaceutical composition may be formulated conventionally with one or more physiologically acceptable carriers including excipients and adjuvants which facilitate processing of the active compound into a pharmaceutically acceptable preparation. The suitable preparation will depend on the route of administration. Any of the well-known techniques, carriers and excipients can be suitably employed, as understood in the art.

The pharmaceutical composition according to the present invention refers to a mixture of any compound in the Compound Examples described herein with other chemical components, such as a carrier, a stabilizer, an antioxidant, a disintegrant, a diluent, a dispersant, a filler, a flavoring agent, a suspending agent, a glidant, a solubilizer, a surfactant, a wetting agent, a thickener and/or an excipient. The pharmaceutical composition facilitates administration of the compound to an organism. During the implement of the treatment or use method provided herein, a therapeutically effective amount of the compound described herein is administered, as a pharmaceutical composition, to a mammal having a disease, disorder or condition to be treated. Preferably, the mammal is a human. The therapeutically effective amount can vary widely, depending on the severity of the disease, the age and relative health status of the subject, the efficacy of the compound used, and so on. The compound may be used alone or in combination with one or more therapeutic agents that are components of a mixture therewith.

The pharmaceutical composition will include, as an active ingredient, at least one of the compounds described in the present invention in the form of a free acid or a free base, or in the form of a pharmaceutically acceptable salt. Additionally, the method and pharmaceutical composition described herein include the use of an N-oxide, a crystalline form (also known as a polymorph), and an active metabolite of these compounds having the same type of activity. In some cases, the compound may exist as a tautomer. All tautomers are contained within the scope of the compound provided in the present invention. Furthermore, the compound described herein may exist as a non-solvate or solvate with a pharmaceutically acceptable solvent such as water, ethanol, and the like. The solvate of the compound provided in the present invention is also deemed to be disclosed herein.

In another aspect, the present invention provides a pharmaceutical preparation including, as an active ingredient, the diphenylaminopyrimidine and triazine compound, or a pharmaceutically acceptable salt, stereoisomer, hydrate or solvate thereof. The pharmaceutical preparation described herein can be administered to a subject by a variety of routes of administration including, but not limited to, oral, parenteral (e.g., intravenous, subcutaneous, and intramuscular), intranasal, buccal, topical, rectal or transdermal administration. The pharmaceutical preparation described herein includes, but is not limited to, aqueous dispersions, self-emulsifying dispersions, solid solutions, liposome dispersions, aerosols, solid dosage forms, powders, immediate-release preparations, controlled-release preparations, fast-dissolving preparations, tablets, capsules, pills, sustained-release preparations, extended-release preparations, pulsed-release preparations, multiparticulate preparations and mixed immediate- and controlled-release preparations.

Pharmaceutical preparations for oral administration can be obtained by mixing one or more solid excipients with one or more of the compounds described herein, and optionally grinding the resulting mixture. If necessary, the mixture is granulated after suitable adjuvants are added, to obtain a tablet or dragee core. Suitable excipients include, for example, fillers such as sugars, including lactose, sucrose, mannitol or sorbitol, and the like; cellulose preparations such as corn starch, wheat starch, rice starch, potato starch, gelatin, tragacanth, methylcellulose, microcrystalline cellulose, hydroxypropylmethylcellulose, and sodium carboxymethylcellulose, etc.; and surfactants such as polyvinylpyrrolidone (PVP or Polyvidone) or calcium phosphate. If desired, a disintegrant such as croscarmellose sodium, polyvinylpyrrolidone, agar or alginic acid or a salt thereof such as sodium alginate may be added.

Pharmaceutical preparations which can be administered orally include push-fit capsules made of gelatin, as well as soft, sealed capsules made of gelatin and a plasticizer such as glycerol or sorbitol. The push-fit capsules may contain the active ingredient in admixture with a filler such as lactose, a binder such as a starch, and/or a lubricant such as talc or magnesium stearate and, optionally, a stabilizer. In soft capsules, the active compound may be dissolved or suspended in a suitable liquid, such as a fatty oil, liquid paraffin, or liquid polyethylene glycols. In addition, a stabilizer may be added. All preparations for oral administration should be in a dosage form suitable for such a route of administration.

In some embodiments, the solid dosage forms disclosed herein may be in the form of tablets (including suspension tablets, fast-dissolving tablets, orally disintegrating tablets, rapidly disintegrating tablets, effervescent tablets or caplets), pills, powders (including aseptically packaged powders, non-essential powders or effervescent powders), capsules (including soft capsules or hard capsules, such as capsules made from animal-derived gelatin, capsules made from plant-derived HPMC, or "sprinkle capsules"), solid dispersions, solid solutions, bioerodible preparations, controlled-release preparations, pulsed-release dosage forms, multiparticulate dosage forms, pellets, granules or aerosols. In other embodiments, the pharmaceutical preparation is in the form of a powder. In still other embodiments, the pharmaceutical preparation is in the form of a tablet, including but not limited to a fast-dissolving tablet. Additionally, the pharmaceutical preparation described herein may be administered in a single or multi-capsule dosage form. In some embodiments, the pharmaceutical preparation is administered in two, or three, or four capsules or tablets.

The pharmaceutical composition includes at least a preparation of any of the compounds described herein, which is suitable for administration by intramuscular, subcutaneous or intravenous injection, and may include aqueous (in physiologically acceptable sterile water) or non-aqueous solutions, dispersions, suspensions or emulsions, and sterile powder injections for preparing sterile injectable solutions or dispersions. Examples of suitable aqueous and nonaqueous carriers, diluents, solvents or vehicles include water, ethanol, polyols (propylene glycol, polyethylene glycol, glycerol, and cremophor, etc.), suitable mixtures thereof, vegetable oils (e.g. olive oil) and organic esters for injection such as ethyl oleate. Appropriate fluidity can be maintained, for example by coating with, for example, lecithin; by maintaining a desired particle size when the preparation is in the form of a dispersion; or by using a surfactant. Preparations suitable for subcutaneous injection may also contain additives such as preservatives, wetting agents, emulsifying agents and dispersing agents. Microbial growth can be prevented by various antibacterial and antifungal agents, for example, parabens, chlorbutol, phenol, sorbic acid, and the like. An isotonic agent such as sugar, sodium chloride or the like may also be included as required. Prolonged absorption of the injectable dosage form can be achieved by the use of an absorption retarder such as aluminum monostearate and gelatin.

The present invention also relates to various pharmaceutical compositions known in the pharmaceutical arts for intraocular, intranasal and intra-aural delivery. The pharmaceutical formulation comprises an aqueous ophthalmic solution of the active compound, which may exist as an aqueous solution such as an eye drop, or as a gellan gum or hydrogel; an ophthalmic ointment; an ophthalmic suspension, such as microparticles, drug-loading small polymeric particles, a fat-soluble preparation, and microspheres suspended in a liquid medium; and an ophthalmic insert. For the stability and comfortableness, these suitable pharmaceutical preparations are most frequently and preferably prepared into sterile, isotonic and buffered preparations. The pharmaceutical composition can also include drops and sprays which often mimic nasal secretions in many aspects to ensure the maintenance of normal ciliary action. As is well known to those skilled in the art, suitable preparations are most often and preferably isotonic and maintain a mildly buffered pH of 5.5 to 6.5, and most often and preferably include an antimicrobial preservative and a suitable drug stabilizer. The pharmaceutical preparation for intra-aural delivery includes suspensions and ointments for topical application in the ear. Common solvents for these aural preparations include glycerin and water.

The present invention also relates to any of the compounds of the present invention, or a pharmaceutically acceptable salt, stereoisomer, hydrate or solvate thereof, which can be administered to a mammal such as a human by oral, parenteral (intravenous, intramuscular, and subcutaneous etc.), transpulmonary, topical, and transdermal administration. The dose of the compound of the present invention for human may range from about 0.1 mg to about 1000 mg.

In another aspect, the present invention further provides use of any of the compounds or a pharmaceutically acceptable salt, stereoisomer, hydrate, solvate, active metabolite and prodrug thereof in the preparation of a drug, which can be administered alone, or in combination with other therapeutic agents that are drugs for treating cancers, cardiovascular diseases, infection, inflammation, immune diseases, cell proliferative diseases, organ transplantation, viral diseases or metabolic diseases.

The drugs for use in combination include, but are not limited to, doxorubicin, dactinomycin, bleomycin, vinblastine, cisplatin, acivicin, aclarubicin, acodazole hydrochloride, acronine, adozelesin, aldesleukin, hexamethyl melamine, ambomycin, ametantrone acetate, aminoglutethimide, amsacrine, anastrozole, antramycin, asparaginase, asperlicin, azacitidine, azetepa, azotomycin, batimastat, benzodepa, bicalutamide, bisantrene hydrochloride, bisnafide dimethanesulfonate, bizelesin, bleomycin sulfate, brequinar sodium, bropirimine, busulfan, actinomycin C, calusterone, caracemide, carbetimer, carboplatin, carmustine, carubicin hydrochloride, carzelesin, cedefingol, chlorambucil, cirolemycin, cladribine, crisnatol mesylate, cyclophosphamide, cytarabine, dacarbazine, daunorubicin hydrochloride, decitabine, dexormaplatin, dezaguanine, dezaguanine mesilate, diaziquone, doxorubicin, doxorubicin hydrochloride, droloxifene, droloxifene citrate, drostanolone propionate, duazomycin, edatrexate, eflornithine hydrochloride, elsamitrucin, enloplatin, enpromate, epipropidine, erbulozole, esorubicin hydrochloride, estramustine, estramustine sodium phosphate, etanidazole, etoposide, etoposide phosphate, chlorophenethylpyramine, fadrozole hydrochloride, fazarabine, fenretinide, floxuridine, fludarabine phosphate, 5-fluorouracil, flurocitabine, fostrecin, gemcitabine, gemcitabine hydrochloride, capecitabine, bortezomib, carfilzomib, afatinib, avastin, bexarotene, calcitriol, pemetrexed disodium, hydroxy urea, idarubicin hydrochloride; ifosfamide; ilmofosine, interleukin II (including recombinant interleukin II or rIL2), interferon alpha-2a, interferon alpha-2b, interferon alpha-n1, interferon alpha-n3, interferon beta-1a, interferon gamma-1b, isoplatin, irinotecan hydrochloride, lanreotide acetate, letrozole, leuprolide acetate, liarozole hydrochloride, lometrexol sodium, lomustine, losoxantrone hydrochloride, masoprocol, maytansine, chlormethine hydrochloride, megestrol acetate; melengestrol acetate, melphalan, menogaril, mercaptopurine, methotrexate, methotrexate sodium, metoprine, meturedepa, mitindomide, mitocarcin, mitochromine, mitogillin, mitomalcin, mitomycin, mitosper, mitotane, mitoxantrone hydrochloride, mycophenolic acid, nocodazole, nogalamycin, ormaplatin, oxisuran, pegaspargase, peliomycin, neptamustine, peplomycin sulfate, perfosfamide, pipobroman, piposulfan, piroxantrone hydrochloride, plicamycin, plomestane, porfimer sodium, porphyromycin, prednimustine, procarbazine hydrochloride, puromycin, puromycin hydrochloride, pirazofurin, riboprine, rogletimide, safingol, safingol hydrochloride, semustine, simtrazene, sodium phosphonacetyl aspartate, sparsomycin, spirogermanium hydrochloride, spiromustine, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurine, tirapazamine, toremifene citrate, tromethonine acetate, 7-normethandrolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleucinol sulfate, vinorelbine, vinrosidine sulfate, vinzolidine sulfate, vorozole, zeniplatin, zinostatin, zorubicin hydrochloride, mitoxantrone, paclitaxel, procarbazine, thiotepa, angiogenesis inhibitors, camptothecin, dexamethasone, aspirin, acetaminophen, indomethacin, ibuprofen, ketoprofen, meloxicam, corticosteroids and adrenal corticosteroids.

Therapeutic Use

The present invention further relates to use of any of the compounds, or a pharmaceutically acceptable salt, stereoisomer, hydrate or solvate thereof, in the manufacture of a drug, which is an ALK tyrosine kinase inhibitor, or is used to prevent or treat a disease, disorder, or condition that benefits from inhibition of the ALK tyrosine kinase activity. Use of the drug for treating and/or preventing a disease in a mammal, including a human, and use of the compound in inhibiting anaplastic lymphoma kinase (ALK) activity or in treating a disease, disorder, or condition that benefits from inhibition of the ALK tyrosine kinase activity are also provided.

In certain embodiments, examples of anaplastic lymphoma kinase (ALK) mediated diseases or disease states include, but are not limited to, cancers, cell proliferative diseases, inflammation, infection, immune diseases, organ transplantation, viral diseases, cardiovascular diseases or metabolic diseases.

Examples of anaplastic lymphoma kinase (ALK) mediated diseases or disease states that can be treated with the compound of the present invention include, but are not limited to, head cancer, thyroid cancer, neck cancer, eye cancer, skin cancer, oral cancer, laryngeal cancer, esophageal cancer, thoracic cancer, bone cancer, leukaemia, myeloma, lung cancer, head and neck cancer, colon cancer, sigmoid cancer, rectal cancer, colon cancer, nasopharyngeal cancer, stomach cancer, prostate cancer, breast cancer, ovarian cancer, uterine cancer, kidney cancer, liver cancer, pancreatic cancer, bladder cancer, brain cancer, intestinal cancer, heart cancer, adrenal cancer, subcutaneous tissue cancer, lymph node cancer, lymphoma, osteosarcoma, melanoma, malignant glioma, B-cell proliferative disease, for example, diffuse large B-cell lymphoma, follicular lymphoma, chronic lymphocytic lymphoma, chronic lymphocytic leukemia, B-cell pro-lymphocytic leukemia, lymphoplasmacytic lymphoma/Waldenstrom macroglobulinemia, splenic marginal zone lymphoma, plasma cell myeloma, plasmacytoma, extranodal marginal zone B-cell lymphoma, marginal zone B-cell lymphoma in lymph nodes, mantle cell lymphoma, mediastinal (thymic) large B-cell lymphoma, intravascular large B-cell lymphoma, primary exudative lymphoma, Burkitt's lymphoma/leukemia or lymphomatoid granulomatosis.

In another preferred embodiment, the cancer is non-small cell lung cancer.

In another preferred embodiment, the cancer is leukemia and lymphoma.

In another preferred embodiment, the immune diseases or inflammation included in the examples of anaplastic lymphoma kinase (ALK) mediated diseases or disease states that can be treated with the compound of the present invention include, but are not limited to, rheumatoid arthritis, osteoarthritis, rheumatoid spondylitis, gout, asthma, bronchitis, rhinitis, chronic obstructive pulmonary disease, cystic fibrosis, and so on.

The present invention provides a method for inhibiting ALK kinase and a method for treating an ALK kinase-related disease, comprising the steps of: administering a compound according to the first aspect of the present invention or a pharmaceutically acceptable salt, hydrate or solvate thereof, or a pharmaceutical composition according to the third aspect of the invention to a subject in need thereof. It should be understood that within the scope of the present invention, the technical features described above and the technical features specifically described in the embodiments may be combined with each other to constitute a new or preferred technical solution, which are not detailed herein for the sake of simplicity.

By means of the above technical solutions, the present invention has the following advantages.

The present invention discloses a diphenylaminopyrimidine and triazine compound of Formula I, and a pharmaceutically acceptable salt, stereoisomer, hydrate or solvate thereof. The diphenylaminopyrimidine and triazine compound of the present invention can be used for treating and/or preventing diseases or conditions associated with inhibition of ALK tyrosine kinase activity, such as cell proliferative diseases, cancers, immune diseases and so on. Compared with the reported ALK inhibitors, this series of compounds have better in-vitro and in-vivo activity and efficacy, and also exhibit obvious advantages in terms of the dosage administered. Therefore, the diphenylaminopyrimidine and triazine compound of the present application has promising prospect and market potential.

DETAILED DESCRIPTION OF THE PREFERRED EMBODIMENTS

The invention will be further illustrated in more detail with reference to embodiments. It is noted that, the following embodiments only are intended for purposes of illustration, but are not intended to limit the scope of the present invention.

I. Preparation of Compounds

1. Synthesis of Compound IX

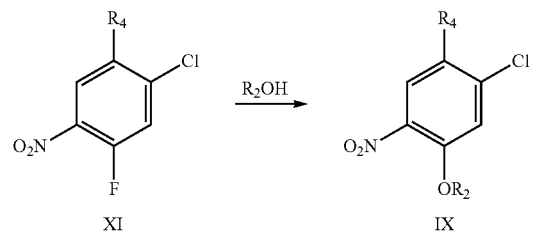

Compound XI was subjected to a substitution reaction to obtain Compound IX. The result is shown in Table 1.

TABLE 1

Structure of Compound IX

| No. | $R_2$ | $R_4$ | LC-MS (M + 1) |
|---|---|---|---|
| 1 | $CD_3$ | H | 191.0 |
| 2 | $CD_3$ | $CH_3$ | 205.0 |
| 3 | $CD_3$ | F | 209.0 |
| 4 | $CD_3$ | Cl | 225.0 |
| 5 | $CD_3$ | $CF_3$ | 259.0 |
| 6 | $CD_3$ | CN | 216.0 |

TABLE 1-continued

| Structure of Compound IX | | | |
|---|---|---|---|
| No. | $R_2$ | $R_4$ | LC-MS (M + 1) |
| 7 | $CD_2CD_3$ | H | 207.1 |
| 8 | $CD_2CD_3$ | $CH_3$ | 221.1 |
| 9 | $CD_2CD_3$ | Cl | 241.0 |

Embodiment 1

Synthesis of Compound IX-1 (where $R_2$=H, and $R_4$=$CD_3$)

Under a nitrogen atmosphere, Compound (XI-1, where $R_4$=$CD_3$)(2.3 g, 13.1 mmol) was added to DMSO (25 mL), and then cesium carbonate (20.8 g, 65.9 mmol) was added to the resulting solution. Deuterated methanol (2.0 mL) was added dropwise at room temperature, and the resulting mixture was heated to 50° C., and reacted for 1 hr, until the reaction was complete as monitored by TLC. The reaction solution was poured into iced water and extracted twice with ethyl acetate. Then the organic phase was dried. The organic solvent was removed by evaporation to obtain a solid. The solid was then recrystallized in methyl t-butyl ether, to obtain Compound (IX-1) (2.0 g, 80%). $^1$H NMR (400 MHz, DMSO-$d_6$): δ=7.92 (d, 1H, J=6.8 Hz), 7.46 (s, 1H), 7.30 (d, 1H, J=6.8 Hz); LC-MS: m/z=191.0 (M+1).

Embodiment 2

Synthesis of Compound IX-2 (where $R_2$=Me, and $R_4$=$CD_3$)

Under a nitrogen atmosphere, Compound (XI-2, where $R_4$=Me) (2.5 g, 13.1 mmol) was added to DMSO (25 mL), and then cesium carbonate (20.8 g, 65.9 mmol) was added to the resulting solution. Deuterated methanol (2 mL) was added dropwise at room temperature, and the resulting mixture was heated to 50° C. and reacted for 1 hr, until the reaction was complete as monitored by TLC. The reaction solution was poured into iced water and extracted twice with ethyl acetate. Then the organic phase was dried. After filtering, the organic solvent was removed by evaporation to obtain a solid. The solid was then recrystallized in methyl t-butyl ether, to obtain Compound (IX-2) (2.2 g, 76.9%). $^1$H NMR (400 MHz, DMSO-$d_6$): δ=7.90 (s, 1H), 7.52 (s, 1H), 2.30 (s, 3H); LC-MS: m/z=205.0 (M+1).

Embodiment 3

Synthesis of Compound IX-8 (where $R_2$=Me, and $R_4$=$CD_2CD_3$)

Under a nitrogen atmosphere, Compound (XI-8) (2.5 g, 13.1 mmol) was added to DMSO (25 mL), and then cesium carbonate (20.8 g, 65.9 mmol) was added to the resulting solution. Deuterated ethanol (2 mL) was added dropwise at room temperature, and the resulting mixture was heated to 50° C., and reacted for 1 hr, until the reaction was complete as monitored by TLC. The reaction solution was poured into iced water and extracted twice with ethyl acetate. Then the organic phase was dried. After filtering, the organic solvent was removed by evaporation to obtain a solid. The solid was then recrystallized in methyl t-butyl ether, to obtain Compound (IX-8) (2.4 g, 83.0%). $^1$H NMR (400 MHz, DMSO-$d_6$): δ=7.92 (s, 1H), 7.50 (s, 1H), 2.30 (s, 3H); LC-MS: m/z=221.1 (M+1).

Following the same procedure as shown in Embodiments 1-3, a series of Compounds (IX-1 to 9) were obtained, the structure of which was confirmed by LC-MS. The results are shown in Table 1.

2. Synthesis of Compound VIII

Compound IX and Compound X were subjected to Suzuki coupling to obtain Compound VIII. The reaction route was as follows.

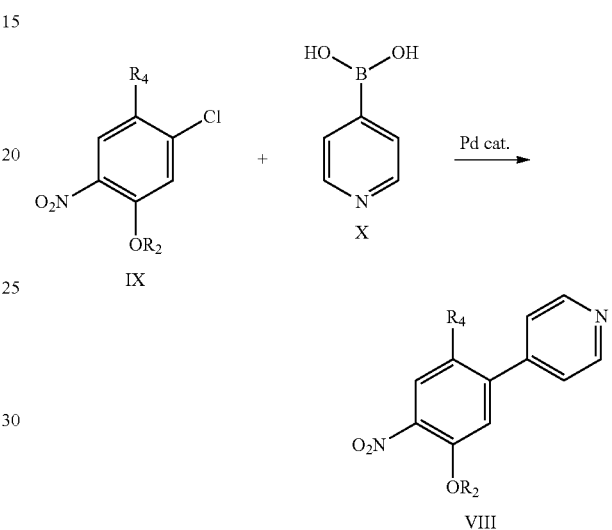

The results are shown in Table 2.

TABLE 2

| Structure of Compound VIII | | | |
|---|---|---|---|
| No. | $R_2$ | $R_4$ | LC-MS (M + 1) |
| 1 | $CD_3$ | H | 234.1 |
| 2 | $CD_3$ | $CH_3$ | 248.1 |
| 3 | $CD_3$ | F | 252.1 |
| 4 | $CD_3$ | Cl | 268.1 |
| 5 | $CD_3$ | $CF_3$ | 302.1 |
| 6 | $CD_3$ | CN | 259.1 |
| 7 | $CD_2CD_3$ | H | 250.1 |
| 8 | $CD_2CD_3$ | $CH_3$ | 264.1 |
| 9 | $CD_2CD_3$ | Cl | 284.1 |

Embodiment 4

Synthesis of Compound VIII-2 (where $R_2$=$CD_3$, and $R_4$=Me)

Under a nitrogen atmosphere, Compound (X) (1.47 g, 12 mmol) was added to a mixed solvent (100 mL/50 mL) of dioxane and water. Tris-(dibenzylideneacetone)dipalladium (1 g, 1.09 mmol), 2-dicyclohexylphosphino-2',6'-dimethoxybiphenyl (1.12 g, 2.72 mmol), Compound (IX-2) (2.5 g, 10.9 mmol) and potassium phosphate (4.62 g, 21.8 mmol) were sequentially added to the mixture, and nitrogen was bubbled for 15 min. The resulting solution was heated to reflux and reacted for 6 hrs, until the reaction was complete as monitored by TLC. The reaction solution was diluted with ethyl acetate (200 mL), and washed with 1 N sodium hydroxide solution at room temperature. The organic solvent was removed by evaporation, and the residue was purified by column chromatography on silica gel to obtain Compound (VIII-2)(1.7 g, 68.8%). $^1$H NMR (400 MHz, DMSO-d$_6$): δ=8.60 (d, 2H, J=7.2 Hz), 8.06 (d, 2H, J=7.0 Hz), 7.96 (s, 1H), 7.50 (s, 1H), 2.30 (s, 3H); LC-MS: m/z=248.1 (M+1).

Embodiment 5

Synthesis of Compound VIII-8 (where R$_2$=CD$_2$CD$_3$, and R$_4$=Me)

Under a nitrogen atmosphere, Compound (X) (1.47 g, 12 mmol) was added to a mixed solvent (100 mL/50 mL) of dioxane and water. Tris-(dibenzylideneacetone)dipalladium [Pd$_2$dba$_3$] (1 g, 1.09 mmol), 2-dicyclohexylphosphino-2',6'-dimethoxybiphenyl (1.12 g, 2.72 mmol), Compound (IX-8) (2.5 g, 10.9 mmol) and potassium phosphate (4.62 g, 21.8 mmol) were sequentially added to the mixture, and nitrogen was bubbled for 15 min. The resulting solution was heated to reflux and reacted for 6 hrs, until the reaction was complete as monitored by TLC. The reaction solution was diluted with ethyl acetate (200 mL), and washed with 1 N sodium hydroxide solution at room temperature. The organic layer was separated, dried, evaporated to remove the organic solvent, and purified by column chromatography on silica gel to obtain Compound (VIII-8)(2.0 g, 62.8%). $^1$H NMR (400 MHz, DMSO-d$_6$): δ=8.62 (d, 2H, J=7.0 Hz), 8.02 (d, 2H, J=7.0 Hz), 7.92 (s, 1H), 7.54 (s, 1H), 2.32 (s, 3H); LC-MS: m/z=264.1 (M+1).

Using the same procedure as shown in Embodiments 4-5, a series of Compounds (VIII-1 to 10) were obtained, the structure of which was confirmed by LC-MS. The results are shown in Table 2.

The coupling reaction of Compound (IX-1) with piperazine and other nitrogen-containing heterocyclic compounds was carried out as follows. The results are shown in Table 3.

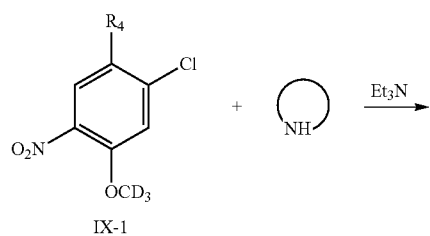

IX-1

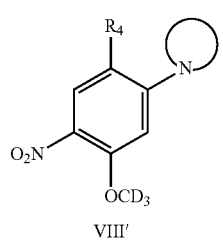

VIII'

TABLE 3

Structure of Compound VIII'

| No. | R$_4$ | Structure | LC-MS (M + 1) |
|---|---|---|---|
| 11 | H | piperidine-4-yl-piperazine-NBoc | 341.2 |
| 12 | H | piperidine-4-yl-thiomorpholine | 341.2 |
| 13 | H | piperidine-N-piperidine-NHBoc | 438.3 |
| 14 | H | piperidine-4-yl-N-methylpiperazine | 338.2 |
| 15 | H | piperidine-4-yl-N,N-dimethylamine | 283.2 |
| 16 | H | piperidine-4-yl-morpholine | 325.2 |
| 17 | Me | piperidine-4-yl-piperazine-NBoc | 355.2 |

Embodiment 6

Synthesis of Compound VIII'-11

The synthesis route of Compound VIII'-11 was as follows.

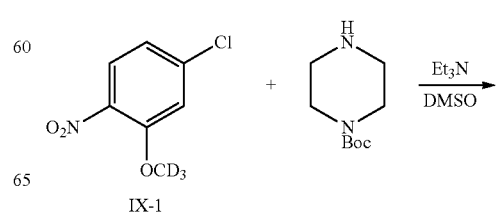

IX-1

-continued

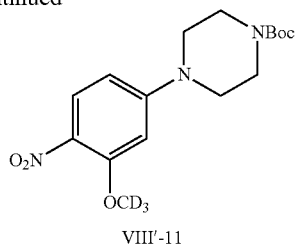

VIII'-11

Compound (IX-1) (3.8 g, 20 mmol) and Boc-piperazine (5.6 g, 30 mmol) were added to DMSO (50 mL) and then triethylamine (3 g, 30 mmol) was added. The resulting solution was heated to 70° C., and reacted for 30 hrs. The reaction solution was cooled to room temperature, stirred with water (100 mL) for 2 hrs to give a precipitate, which was filtered to obtain Compound (VIII'-11) (4.80 g, 70%). $^1$H NMR (400 MHz, DMSO-$d_6$): δ=7.80 (s, 1H, J=7.0 Hz), 6.62 (s, 1H, J=7.0 Hz), 6.50 (s, 1H), 3.32-3.42 (m, 8H), 1.34 (s, 9H); LC-MS: m/z=341.2 (M+1).

Following the same procedure as shown in Embodiment 6, a series of Compounds (VIII'-11 to 17) were obtained, the structure of which was confirmed by LC-MS. The results are shown in Table 3.

3. Synthesis of Compound VII

The synthesis route of Compound VII was as follows.

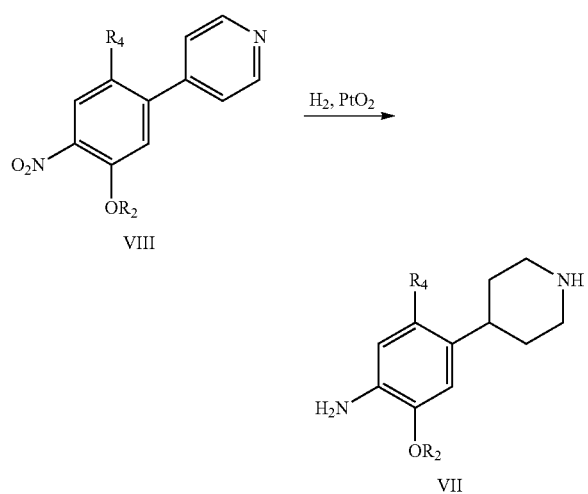

Embodiment 7

Synthesis of Compound VII-2 (where $R_4$=Me, and $R_2$=$CD_3$)

Compound (VIII-2) (4.38 g, 16.1 mmol), trifluoroacetic acid (2.4 ml, 32.2 mmol), and $PtO_2$ (1.76 g, 40%) were added to acetic acid (200 mL), and the resulting solution was reacted under a hydrogen atmosphere for 36 hrs. After the reaction was complete as monitored by TLC, the solid was removed by filtration. The organic solvent in the mother liquid was removed by evaporation, and the solid was dissolved in ethyl acetate. Then, it was washed with a 1 N NaOH solution until pH value is 10, and the organic phase was dried, filtered, and concentrated to give Compound (VII-2) (2.5 g, 70%). $^1$H NMR (400 MHz, DMSO-$d_6$): δ=9.50-8.04 (br, 1H), 6.53 (s, 1H), 6.44 (s, 1H), 4.44 (s, 2H), 3.03-2.96 (m, 2H), 2.87-2.84 (m, 2H), 2.83-2.80 (m, 1H), 2.12 (s, 3H), 1.78-1.72 (m, 4H); LC-MS: m/z=224.2 (M+1).

Embodiment 8

Synthesis of Compound VII-8 (where $R_4$=Me, and $R_2$=$CD_2CD_3$)

Compound (VIII-8) (4.38 g, 16.1 mmol), trifluoroacetic acid (2.4 ml, 32.2 mmol), and $PtO_2$ (1.76 g, 40%) were added to acetic acid (200 mL) and the resulting solution was reacted under a hydrogen atmosphere for 36 hrs. After the reaction was complete as monitored by TLC, the solid was removed by filtration. The solvent was removed by evaporation, and the solid was dissolved in ethyl acetate, and washed with a 1N NaOH solution until pH value is 10. The organic phase was dried, filtered, and concentrated to obtain Compound (VII-8) (2.65 g, 68.8%). $^1$H NMR (400 MHz, DMSO-$d_6$): δ=9.52-8.00 (br, 1H), 6.53 (s, 1H), 6.48 (s, 1H), 4.40 (s, 2H), 3.00-2.92 (m, 2H), 2.84-2.86 (m, 2H), 2.80-2.82 (m, 1H), 2.14 (s, 3H), 1.78-1.70 (m, 4H); LC-MS: m/z=240.2 (M+1).

Using the same procedure as shown in Embodiments 7-8, a series of Compounds (VII-1 to 9) were obtained, the structure of which was confirmed by LC-MS. The results are shown in Table 4.

TABLE 4

| | Structure of Compound VII | | |
|---|---|---|---|
| No. | $R_2$ | $R_4$ | LC-MS (M + 1) |
| 1 | $CD_3$ | H | 210.2 |
| 2 | $CD_3$ | $CH_3$ | 224.2 |
| 3 | $CD_3$ | F | 228.2 |
| 4 | $CD_3$ | Cl | 244.1 |
| 5 | $CD_3$ | $CF_3$ | 278.2 |
| 6 | $CD_3$ | CN | 235.2 |
| 7 | $CD_2CD_3$ | H | 226.2 |
| 8 | $CD_2CD_3$ | $CH_3$ | 240.2 |
| 9 | $CD_2CD_3$ | Cl | 260.2 |

The reduction of the nitrogen-containing heterocyclic Compound (VIII) was carried out according to a reaction route as follows.

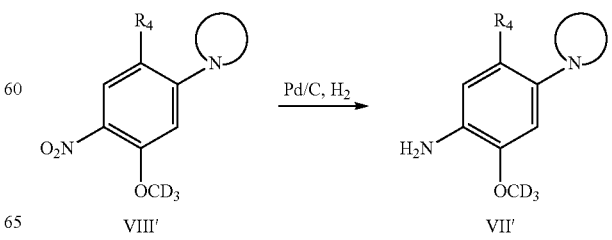

VIII'                                       VII'

Embodiment 9

Synthesis of Compound VII'-11

The synthesis route of Compound VII'-11 was as follows.

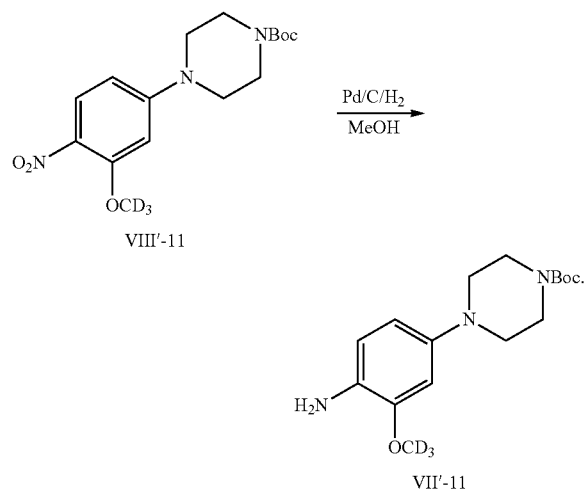

Compound (VIII'-11) (6.8 g, 20 mmol), and 10% Pd/C (0.6 g) were added to methanol (100 mL), and reacted for 26 hrs under a hydrogen atmosphere. After the reaction was complete as monitored by TLC, the solid was removed by filtration. Methanol was concentrated to obtain Compound (VII'-11) (5.7 g, 92%). $^1$H NMR (400 MHz, DMSO-d$_6$): δ=6.48 (s, 1H, J=7.0 Hz), 6.26 (s, 1H, J=7.0 Hz), 6.00 (s, 1H), 3.30-3.40 (m, 8H), 1.34 (s, 9H); LC-MS: m/z=311.2 (M+1).

Following the same procedure as shown in Embodiment 9, a series of Compounds (VII'-1 to 9) were obtained, the structure of which was confirmed by LC-MS. The results are shown in Table 5.

TABLE 5

Structure of nitrogen-containing heterocyclic Compound VII'

| No. | R$_4$ | (structure) | LC-MS (M + 1) |
|---|---|---|---|
| 11 | H | N-piperidine-N'-Boc-piperazine | 311.2 |
| 12 | H | N-piperidine-thiomorpholine | 311.2 |
| 13 | H | N-piperidine-piperidine-NHBoc | 408.3 |
| 14 | H | N-piperidine-N'-methylpiperazine | 308.3 |
| 15 | H | N-piperidine-N(CH$_3$)$_2$ | 253.2 |
| 16 | H | N-piperidine-morpholine | 295.2 |
| 17 | CH$_3$ | N-piperidine-N'-Boc-piperazine | 325.2 |

4. Synthesis of Compound IV

The synthesis route of Compound IV was as follows.

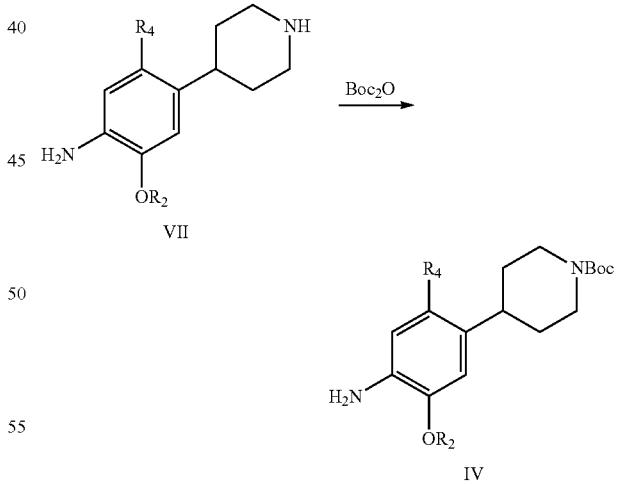

Embodiment 10

Synthesis of Compound IV-2 (where R$_4$=Me, and R$_2$=CD$_3$)

Compound (VII-2) (2.0 g, 9.0 mmol), and triethyl amine (2.2 ml, 15.7 mmol) were dissolved in dichloromethane (100 mL), and cooled to 0° C. Then, di-tert-butyl dicarbonate (1.8 g, 9.0 mmol) was added in one portion, and reacted with stirring. After the reaction was complete as monitored by TLC, the organic solvent was removed by evaporation, and the residue was purified by column chromatography on silica gel to obtain Compound (IV-2) (2 g, 69.0%). $^1$H NMR (400 MHz, CD$_3$OD) δ=7.61 (s, 1H), 6.76 (s, 1H), 4.22 (d, J=13.2 Hz, 2H), 2.90 (m, 3H), 2.28 (s, 3H), 1.73 (d, J=12.2 Hz, 2H), 1.54 (d, J=11.4 Hz, 2H), 1.52 (s, 9H); LC-MS: m/z=324.2 (M+1).

Embodiment 11

Synthesis of Compound IV-8 (where R$_4$=Me, and R$_2$=CD$_2$CD$_3$)

Compound (VII-8) (2.0 g, 9.0 mmol), and triethyl amine (2.2 mL, 15.7 mmol) were dissolved in dichloromethane (100 mL), and cooled to 0° C. Then, di-tert-butyl dicarbonate (1.8 g, 9.0 mmol) was added in one portion, and reacted with stirring. After the reaction was complete as monitored by TLC, the organic solvent was removed by evaporation, and the residue was purified by column chromatography on silica gel to obtain Compound (IV-8) (2.5 g, 81.8%). $^1$H NMR (400 MHz, CD$_3$OD) δ=7.64 (s, 1H), 6.72 (s, 1H), 4.20 (d, J=13.0 Hz, 2H), 2.92 (m, 3H), 2.24 (s, 3H), 1.70 (d, J=12.2 Hz, 2H), 1.52 (d, J=11.4 Hz, 2H), 1.50 (s, 9H); LC-MS: m/z=340.2 (M+1).

Using the same procedure as shown in Embodiments 10-11, a series of Compounds (IV-1 to 9) were obtained, the structure of which was confirmed by LC-MS. The results are shown in Table 6.

TABLE 6

Structure of Compound IV

| No. | R$_2$ | R$_4$ | LC-MS (M + 1) |
|---|---|---|---|
| 1 | CD$_3$ | H | 310.2 |
| 2 | CD$_3$ | CH$_3$ | 324.2 |
| 3 | CD$_3$ | F | 328.2 |
| 4 | CD$_3$ | Cl | 344.1 |
| 5 | CD$_3$ | CF$_3$ | 378.2 |
| 6 | CD$_3$ | CN | 335.2 |
| 7 | CD$_2$CD$_3$ | H | 326.2 |
| 8 | CD$_2$CD$_3$ | CH$_3$ | 340.2 |
| 9 | CD$_2$CD$_3$ | Cl | 360.2 |

5. Synthesis of Compound III

Compound V was coupled to the pyrimidine Compound VI, to obtain Compound III. The reaction route was as follows.

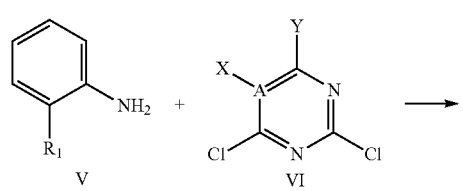

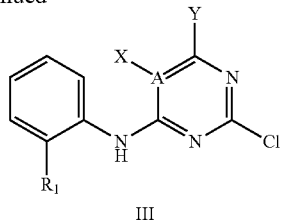

Embodiment 12

Synthesis of Compound III-3

At 0° C. and under a nitrogen atmosphere, NaH (1.51 g, 60%, 37.64 mmol) was added to DMF (50 mL) and DMSO (5 mL), and stirred for 5 min at 0° C. Then, a solution of Compound (V-3, where R$_1$=i-PrSO$_2$)(5 g, 25.09 mmol) in DMF/DMSO (18 mL/2 mL) was added dropwise to the mixed solution, and stirred for 45 min while the temperature was maintained at 0° C. A solution of 2, 4, 5-tricloropyrimidine (111-3) (9.20 g, 50.18 mmol) in DMF/DMSO (18 mL/2 mL) was added dropwise to the mixed solution. The resulting solution was stirred at 0° C. for 45 min and then at room temperature for 2 hrs. After the reaction was complete as monitored by TLC, the reaction solution was poured into iced water, and extracted twice with ethyl acetate. The organic solvent was removed by evaporation, and the residue was purified by column chromatography on silica gel to obtain Compound III-3 (5.2 g, 60.6%). $^1$H NMR (400 MHz, DMSO-d$_6$): δ=9.81 (s, 1H), 8.57 (s, 1H), 8.32 (d, J=8.3 Hz, 1H), 7.96-7.82 (m, 2H), 7.56-7.42 (m, 1H), 3.61-3.46 (m, 1H), 1.16 (d, J=6.8 Hz, 6H); LC-MS: m/z=346.0 (M+1).

Using the same procedure as shown in Embodiment 12, a series of Compounds (III-1 to 19) were obtained, the structure of which was confirmed by LC-MS. The results are shown in Table 7.

TABLE 7

Structure of Compound III

| No. | R1: | A | X | Y | LC-MS (M + 1) |
|---|---|---|---|---|---|
| 1 | i-PrSO$_2$ | C | H | H | 312.1 |
| 2 | i-PrSO$_2$ | C | F | H | 330.0 |
| 3 | i-PrSO$_2$ | C | Cl | H | 346.0 |
| 4 | i-PrSO$_2$ | C | Br | H | 390.0 |
| 5 | i-PrSO$_2$ | C | CF$_3$ | H | 380.0 |
| 6 | i-PrSO$_2$ | C | CN | H | 337.0 |
| 7 | i-PrSO$_2$ | C | OMe | H | 342.1 |
| 8 | i-PrSO$_2$ | C | Me | H | 326.1 |
| 9 | i-PrSO$_2$ | C | Et | H | 340.1 |
| 10 | i-PrSO$_2$ | C | NO$_2$ | H | 357.0 |
| 11 | i-PrSO$_2$ | C | Ph | H | 388.1 |
| 12 | i-PrSO$_2$ | C |  | H | 338.1 |
| 13 | i-PrSO$_2$ | C |  | H | 336.1 |

TABLE 7-continued

Structure of Compound III

| No. | R1: | A | X | | Y | LC-MS (M + 1) |
|---|---|---|---|---|---|---|
| 14 | i-PrSO$_2$ | C | $\stackrel{Y}{\underset{X}{C}}$ = | (pyrrole-NH substituent) | / | 351.1 |
| 15 | i-PrSO$_2$ | C | $\stackrel{Y}{\underset{X}{C}}$ = | (pyrrole-NH substituent) | / | 351.1 |
| 16 | i-PrSO$_2$ | C | $\stackrel{Y}{\underset{X}{C}}$ = | (thiophene substituent) | / | 368.0 |
| 17 | i-PrSO$_2$ | C | $\stackrel{Y}{\underset{X}{C}}$ = | (thiophene substituent) | / | 368.0 |
| 18 | i-PrSO$_2$ | C | $\stackrel{Y}{\underset{X}{C}}$ = | (phenyl substituent) | / | 362.1 |
| 19 | Me$_2$P(O) | C | Cl | | H | 316.0 |
| 20 | i-PrSO$_2$ | N | / | | H | 313.0 |

6. Synthesis of Compound II

In the presence of a palladium catalyst, Compound III was coupled to Compound VI, to obtain Compound II. The reaction route was as follows.

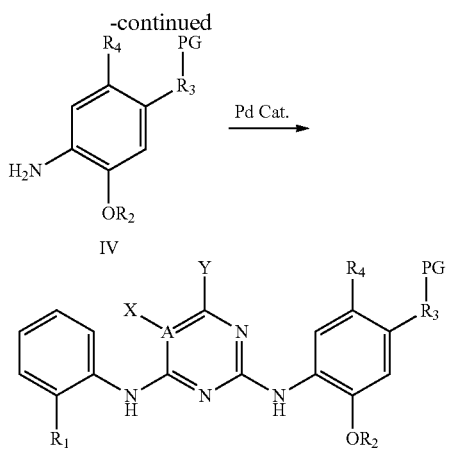

Embodiment 13

Synthesis of Compound II-3

Under a nitrogen atmosphere, Compound (IV-2) (1.7 g, 4.8 mmol), Compound (III-3) (1.69 g, 4.88 mmol), 4,5-Bis(diphenylphosphino)-9,9-dimethylxanthene (Xantphos) (280 mg, 0.49 mmol), palladium acetate (55 mg, 0.25 mmol), and cesium carbonate (4.77 g, 14.6 mmol) were added to tetrahydrofuran, and heated to reflux and reacted for 36 hrs. After the reaction was complete as monitored by TLC, the organic solvent was removed by evaporation, and the residue was purified by column chromatography on silica gel to obtain Compound (II-3)(2.1 g, 69.3%). $^1$H NMR (400 MHz, DMSO-d$_6$): δ=8.30 (s, 1H), 8.27 (d, J=7.2 Hz, 1H), 7.84 d, J=7.2 Hz, 1H), 7.65 (dd, J=7.2 Hz, 7.0 Hz, 1H), 7.44 (dd, J=7.2 Hz, 7.0 Hz, 1H), 7.40 (s, 1H), 6.80 (s, 1H), 3.49-3.32 (m, 3H), 3.10-2.91 (m, 3H), 2.09 (s, 3H), 1.89-1.77 (m, 4H), 1.36 (s, 9H), 1.13 (d, 6H); LC-MS: m/z=633.3 (M+1).

Embodiment 14

Synthesis of Compound II-16

Under a nitrogen atmosphere, Compound (IV-12) (1.5 g, 4.8 mmol), Compound (III-3) (1.69 g, 4.88 mmol), 4,5-Bis(diphenylphosphino)-9,9-dimethylxanthene (Xantphos) (280 mg, 0.49 mmol, 0.1 eq), palladium acetate (55 mg, 0.25 mmol), and cesium carbonate (4.77 g, 14.6 mmol) were added to tetrahydrofuran, and heated to reflux and reacted for 40 hrs. After the reaction was complete as monitored by TLC, the organic solvent was removed by evaporation, and the residue was purified by column chromatography on silica gel to obtain Compound (II-16)(1.8 g, 72%). $^1$H NMR (400 MHz, DMSO-d$_6$): δ=8.32 (s, 1H), 8.24 (d, J=7.2 Hz, 1H), 7.82 (d, J=7.2 Hz, 1H), 7.65 (dd, J=7.2 Hz, 7.0 Hz, 1H), 7.40 (dd, J=7.2 Hz, 7.0 Hz, 1H), 7.32 (d, J=6.8 Hz, 1H), 6.80 (s, 1H), 3.20-3.32 (m, 9H), 1.36 (s, 9H), 1.13 (d, 6H); LC-MS: m/z=620.2 (M+1).

Using the same procedure as shown in embodiments 13-14, a series of Compounds (11-1 to 43) were obtained, the structure of which was confirmed by LC-MS. The results are shown in Table 8.

TABLE 8
Structure of Compound II
| No. | R₁ | A | X | Y | R₂ | R₄ | R₃-PG | LC-MS (M + 1) |
|---|---|---|---|---|---|---|---|---|
| 1 | i-PrSO₂ | C | H | H | CD₃ | Me | 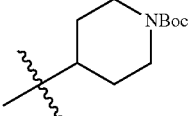 | 599.3 |
| 2 | i-PrSO₂ | C | F | H | CD₃ | Me | 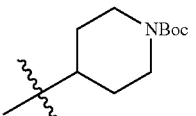 | 617.3 |
| 3 | i-PrSO₂ | C | Cl | H | CD₃ | Me | 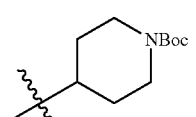 | 633.3 |
| 4 | i-PrSO₂ | C | Br | H | CD₃ | Me | 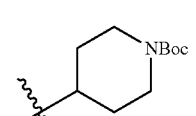 | 677.2 |
| 5 | i-PrSO₂ | C | CF₃ | H | CD₃ | Me | 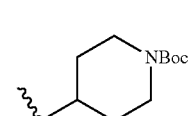 | 667.3 |
| 6 | i-PrSO₂ | C | CN | H | CD₃ | Me | 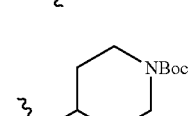 | 624.3 |
| 7 | i-PrSO₂ | C | OMe | H | CD₃ | Me | 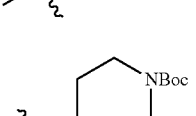 | 629.3 |
| 8 | i-PrSO₂ | C | Me | H | CD₃ | Me | 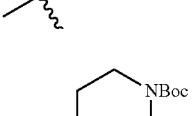 | 613.3 |
| 9 | i-PrSO₂ | C | Et | H | CD₃ | Me | 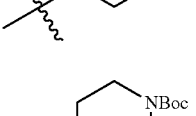 | 627.3 |
| 10 | i-PrSO₂ | C | NO₂ | H | CD₃ | Me | 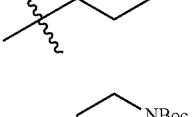 | 644.3 |

TABLE 8-continued
Structure of Compound II
| No. | R₁ | A | X | Y | R₂ | R₄ | R₃-PG | LC-MS (M + 1) |
|---|---|---|---|---|---|---|---|---|
| 11 | i-PrSO₂ | C | Ph | H | CD₃ | Me | 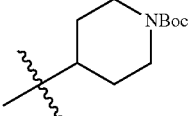 | 675.3 |
| 12 | i-PrSO₂ | C | 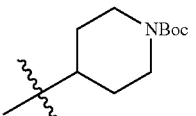 | H | CD₃ | Me | 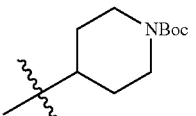 | 625.3 |
| 13 | i-PrSO₂ | C | 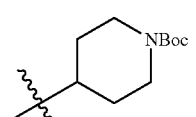 | H | CD₃ | Me | 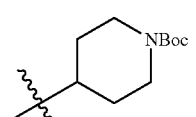 | 623.3 |
| 14 | i-PrSO₂ | C | Cl | H | CD₂CD₃ | Me | 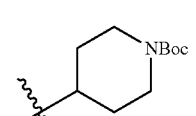 | 649.3 |
| 15 | i-PrSO₂ | C | Cl | H | CD₃ | H | 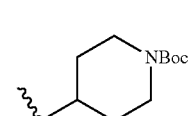 | 619.3 |
| 16 | i-PrSO₂ | C | Cl | H | CD₃ | H | 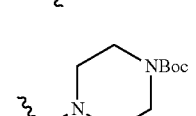 | 620.2 |
| 17 | i-PrSO₂ | C | Cl | H | CD₃ | Me | 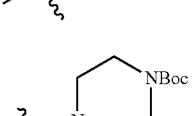 | 634.3 |
| 18 | i-PrSO₂ | C | Cl | H | CD₃ | Cl | 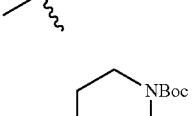 | 653.2 |
| 19 | i-PrSO₂ | C | Cl | H | CD₂CD₃ | Cl | 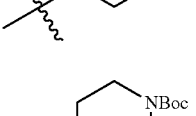 | 669.2 |
| 20 | i-PrSO₂ | C | Cl | H | CD₂CD₃ | H | 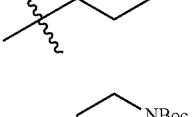 | 635.3 |

TABLE 8-continued
Structure of Compound II
| No. | R$_1$ | A | X | Y | R$_2$ | R$_4$ | R$_3$-PG | LC-MS (M + 1) |
|---|---|---|---|---|---|---|---|---|
| 21 | i-PrSO$_2$ | C | Cl | H | CD$_3$ | F | 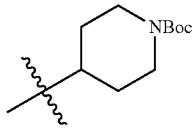 [SMILES: *C1CCN(C(=O)OC(C)(C)C)CC1] | 637.2 |
| 22 | i-PrSO$_2$ | C | Cl | H | CD$_3$ | CF$_3$ | 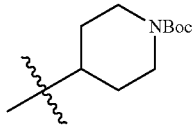 [SMILES: *C1CCN(C(=O)OC(C)(C)C)CC1] | 687.2 |
| 23 | i-PrSO$_2$ | C | Cl | H | CD$_3$ | CN | 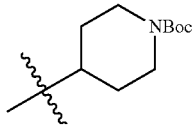 [SMILES: *C1CCN(C(=O)OC(C)(C)C)CC1] | 644.2 |
| 24 | i-PrSO$_2$ | C | 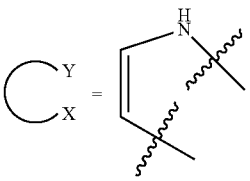 | / | CD$_3$ | H | 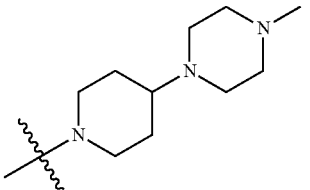 [SMILES: *N1CCC(N2CCN(C)CC2)CC1] | 622.3 |
| 25 | i-PrSO$_2$ | C | 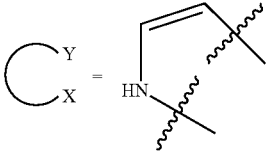 | / | CD$_3$ | H | 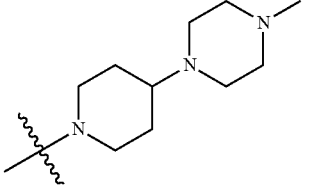 [SMILES: *N1CCC(N2CCN(C)CC2)CC1] | 622.3 |
| 26 | i-PrSO$_2$ | C | 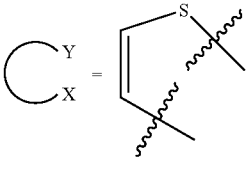 | / | CD$_3$ | H | 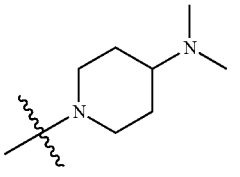 [SMILES: *N1CCC(N(C)C)CC1] | 584.2 |
| 27 | i-PrSO$_2$ | C | 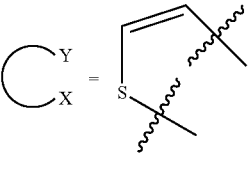 | / | CD$_3$ | H | 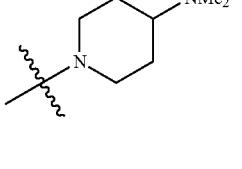 | 584.2 |
| 28 | i-PrSO$_2$ | C | 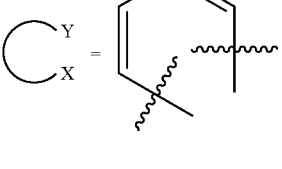 | / | CD$_3$ | H | 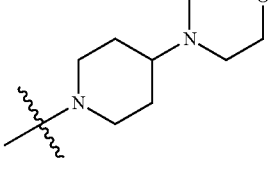 | 620.3 |

TABLE 8-continued

Structure of Compound II

| No. | R₁ | A | X | Y | R₂ | R₄ | R₃-PG | LC-MS (M + 1) |
|---|---|---|---|---|---|---|---|---|
| 29 | i-PrSO₂ | C | | / | CD₃ | Me | | 649.3 |
| 30 | i-PrSO₂ | C | | / | CD₃ | Me | | 638.3 |
| 31 | i-PrSO₂ | C | | / | CD₃ | Me | | 638.3 |
| 32 | i-PrSO₂ | C | | / | CD₃ | Me | | 655.3 |
| 33 | i-PrSO₂ | C | Cl | H | CD₃ | H | | 620.2 |
| 34 | i-PrSO₂ | C | Cl | H | CD₃ | H | | 717.3 |
| 35 | i-PrSO₂ | C | Cl | H | CD₃ | H | | 604.3 |
| 36 | i-PrSO₂ | C | Cl | H | CD₃ | H | | 617.3 |

TABLE 8-continued
Structure of Compound II
| No. | R₁ | A | X | Y | R₂ | R₄ | R₃-PG | LC-MS (M + 1) |
|---|---|---|---|---|---|---|---|---|
| 37 | Me₂P(O) | C | Cl | H | CD₃ | H | 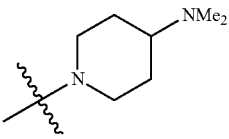 [SMILES: *N1CCC(N(C)C)CC1] | 532.2 |
| 38 | Me₂P(O) | C | Cl | H | CD₃ | Me | 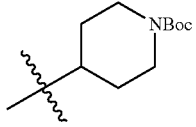 | 603.3 |
| 39 | i-PrSO₂ | N | / | H | CD₃ | H | 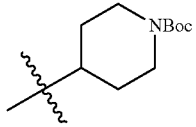 [SMILES: *C1CCN(C(=O)OC(C)(C)C)CC1] | 586.3 |
| 40 | i-PrSO₂ | N | / | H | CD₃ | Me | 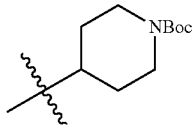 [SMILES: *C1CCN(C(=O)OC(C)(C)C)CC1] | 600.3 |
| 41 | i-PrSO₂ | N | / | H | CD₃ | H | 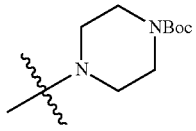 [SMILES: *N1CCN(C(=O)OC(C)(C)C)CC1] | 587.3 |
| 42 | i-PrSO₂ | N | / | H | CD₃ | Me | 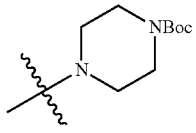 [SMILES: *N1CCN(C(=O)OC(C)(C)C)CC1] | 601.3 |
| 43 | i-PrSO₂ | N | / | H | CD₃ | H | 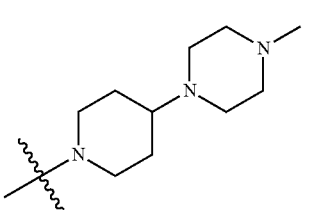 [SMILES: *N1CCC(N2CCN(C)CC2)CC1] | 584.3 |

7. Synthesis of Compound I

Compound II protected with a Boc group was deprotected, and then subjected to a salt formation reaction with a hydrogen chloride-ethanol solution to obtain a hydrochloride of the target Compound (I) of Formula (I). If no protecting group was present in Compound II, the salt formation reaction with the hydrogen chloride-ethanol solution was carried out directly without the deprotection reaction. The reaction route was as follows.

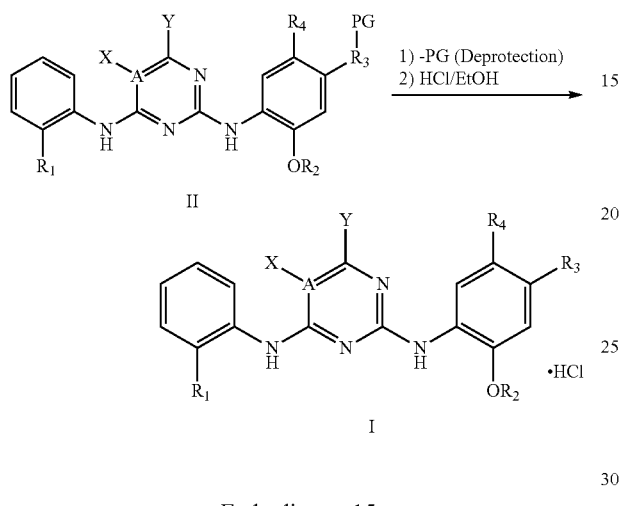

Embodiment 15

Synthesis of Compound I-3

Compound (11-3) (2.1 g, 3.3 mmol) was added to a solution of dichloromethane (10 mL) and trifluoroacetic acid (10 mL), and stirred at room temperature for 2 hrs. After the reaction was complete as monitored by TLC, the organic solvent was removed by evaporation, and the residue was dissolved in dichloromethane (100 mL), washed with a saturated sodium carbonate solution, dried, filtered and concentrated, to obtain a free amine. The free amine product was dissolved in dichloromethane (20 mL), a hydrogen chloride/ethanol solution (4 M, 10 mL) was added, and then the resulting solution was stirred at room temperature for 2 hrs. A white solid was precipitated, filtered under suction, and dried to obtain Compound (1-3) (1.8 g, 95.2%). $^1$H NMR (400 MHz, DMSO-$d_6$) δ=8.32 (s, 1H), 8.27 (d, J=7.2 Hz, 1H), 7.88 (d, J=7.2 Hz, 1H), 7.67 (dd, J=7.2 Hz, 7.0 Hz, 1H), 7.45 (dd, J=7.2 Hz, 7.0 Hz, 1H), 7.42 (s, 1H), 6.79 (s, 1H), 3.49-3.32 (m, 3H), 3.10-2.91 (m, 3H), 2.09 (s, 3H), 1.89-1.77 (m, 4H), 1.13 (d, 6H); LC-MS: m/z=533.3 (M+1).

Embodiment 16

Synthesis of Compound 1-16

Compound (11-16) (1.7 g, 3.3 mmol) was added to a solution of dichloromethane (10 mL) and trifluoroacetic acid (10 mL), and stirred at room temperature for 3 hrs. After the reaction was complete as monitored by TLC, the organic solvent was removed by evaporation, and the residue was then dissolved in dichloromethane (100 mL), washed with a saturated sodium carbonate solution, dried, filtered and concentrated, to obtain a free amine. The free amine product was dissolved in dichloromethane (20 mL), a hydrogen chloride/ethanol solution (4 M, 10 mL) was added, and then stirred at room temperature for 2 hrs. A white solid was precipitated, filtered under suction, and dried to obtain Compound (1-16) (1.4 g, 96%). $^1$H NMR (400 MHz, DMSO-$d_6$): δ=8.30 (s, 1H), 8.20 (d, J=7.2 Hz, 1H), 7.82 (d, J=7.2 Hz, 1H), 7.62 (dd, J=7.2 Hz, 7.0 Hz, 1H), 7.42 (dd, J=7.2 Hz, 7.0 Hz, 1H), 7.36 (d, J=6.8 Hz, 1H), 6.80 (s, 1H), 3.20-3.32 (m, 9H), 1.13 (d, 6H); LC-MS: m/z=520.2 (M+1).

Using the same procedure as shown in embodiments 15-16, a series of Compounds (I-1 to 43) were obtained, the structure of which was confirmed by LC-MS. The results are shown in Table 9.

TABLE 9

Structure of Compound I

| No. | R1: | A | X | Y | $R_2$ | $R_4$ | $R_3$ | LC-MS (M + 1) |
|---|---|---|---|---|---|---|---|---|
| 1 | i-PrSO$_2$ | C | H | H | CD$_3$ | Me | 4-piperidinyl (NH) | 499.3 |
| 2 | i-PrSO$_2$ | C | F | H | CD$_3$ | Me | 4-piperidinyl (NH) | 517.3 |
| 3 | i-PrSO$_2$ | C | Cl | H | CD$_3$ | Me | 4-piperidinyl (NH) | 533.3 |

TABLE 9-continued
Structure of Compound I
| No. | R1: | A | X | Y | R$_2$ | R$_4$ | R$_3$ | LC-MS (M + 1) |
|---|---|---|---|---|---|---|---|---|
| 4 | i-PrSO$_2$ | C | Br | H | CD$_3$ | Me | 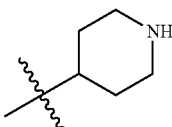 | 577.2 |
| 5 | i-PrSO$_2$ | C | CF$_3$ | H | CD$_3$ | Me | 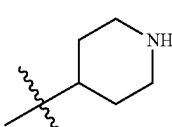 | 567.3 |
| 6 | i-PrSO$_2$ | C | CN | H | CD$_3$ | Me | 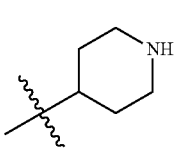 [SMILES: *C1CCNCC1] | 524.3 |
| 7 | i-PrSO$_2$ | C | OMe | H | CD$_3$ | Me | 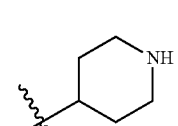 | 529.3 |
| 8 | i-PrSO$_2$ | C | Me | H | CD$_3$ | Me | 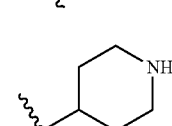 | 513.3 |
| 9 | i-PrSO$_2$ | C | Et | H | CD$_3$ | Me | 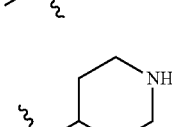 | 527.3 |
| 10 | i-PrSO$_2$ | C | NO$_2$ | H | CD$_3$ | Me | 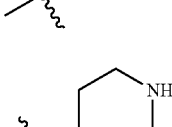 | 544.3 |
| 11 | i-PrSO$_2$ | C | Ph | H | CD$_3$ | Me | 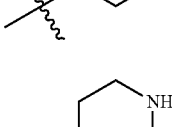 | 575.3 |
| 12 | i-PrSO$_2$ | C | 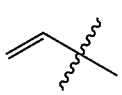 [SMILES: *C=C] | H | CD$_3$ | Me | 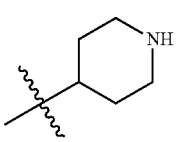 [SMILES: *C1CCNCC1] | 525.3 |
| 13 | i-PrSO$_2$ | C |  | H | CD$_3$ | Me | 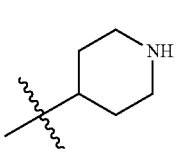 [SMILES: *C1CCNCC1] | 523.3 |

TABLE 9-continued
Structure of Compound I
| No. | R1: | A | X | Y | R$_2$ | R$_4$ | R$_3$ | LC-MS (M + 1) |
|---|---|---|---|---|---|---|---|---|
| 14 | i-PrSO$_2$ | C | Cl | H | CD$_2$CD$_3$ | Me | 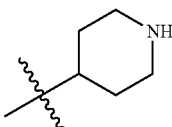 | 549.3 |
| 15 | i-PrSO$_2$ | C | Cl | H | CD$_3$ | H | 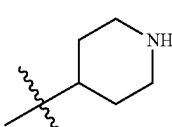 | 519.3 |
| 16 | i-PrSO$_2$ | C | Cl | H | CD$_3$ | H | 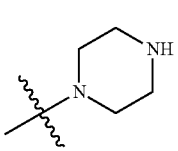 [SMILES: *N1CCNCC1] | 520.2 |
| 17 | i-PrSO$_2$ | C | Cl | H | CD$_3$ | Me | 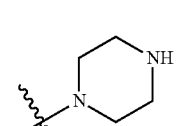 | 534.3 |
| 18 | i-PrSO$_2$ | C | Cl | H | CD$_3$ | Cl | 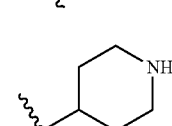 | 553.2 |
| 19 | i-PrSO$_2$ | C | Cl | H | CD$_2$CD$_3$ | Cl | 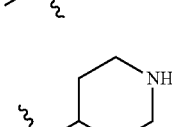 | 569.2 |
| 20 | i-PrSO$_2$ | C | Cl | H | CD$_2$CD$_3$ | H | 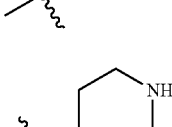 | 535.2 |
| 21 | i-PrSO$_2$ | C | Cl | H | CD$_3$ | F | 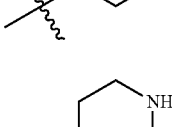 | 537.2 |
| 22 | i-PrSO$_2$ | C | Cl | H | CD$_3$ | CF$_3$ | 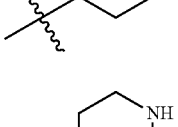 | 587.2 |
| 23 | i-PrSO$_2$ | C | Cl | H | CD$_3$ | CN | 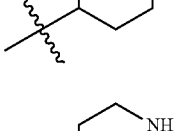 | 544.3 |

TABLE 9-continued
Structure of Compound I
| No. | R1: | A | X | Y | R₂ | R₄ | R₃ | LC-MS (M + 1) |
|---|---|---|---|---|---|---|---|---|
| 24 | i-PrSO₂ | C | 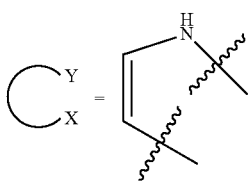 | / | CD₃ | H | 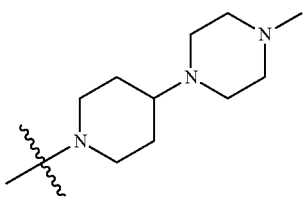 [SMILES: *N1CCC(N2CCN(C)CC2)CC1] | 622.3 |
| 25 | i-PrSO₂ | C | 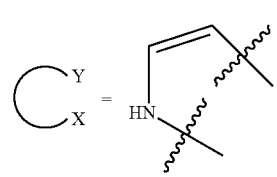 | / | CD₃ | H | 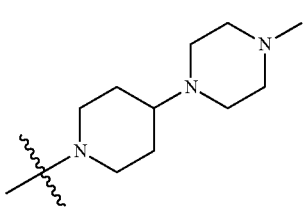 [SMILES: *N1CCC(N2CCN(C)CC2)CC1] | 622.3 |
| 26 | i-PrSO₂ | C | 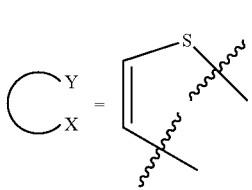 | / | CD₃ | H | 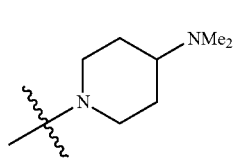 [SMILES: *N1CCC(N(C)C)CC1] | 584.2 |
| 27 | i-PrSO₂ | C | 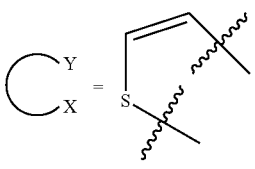 | / | CD₃ | H | 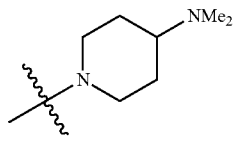 [SMILES: *N1CCC(N(C)C)CC1] | 584.2 |
| 28 | i-PrSO₂ | C | 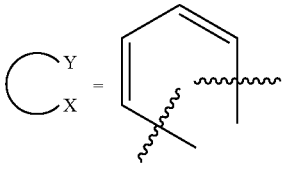 | / | CD₃ | H | 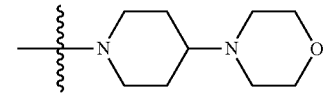 [SMILES: *N1CCC(N2CCOCC2)CC1] | 620.3 |
| 29 | i-PrSO₂ | C | 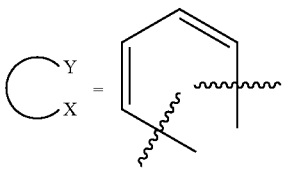 | / | CD₃ | Me | 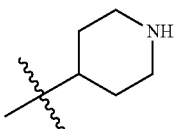 | 549.3 |
| 30 | i-PrSO₂ | C | 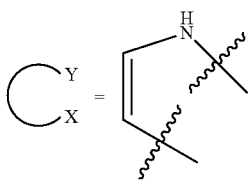 | / | CD₃ | Me | 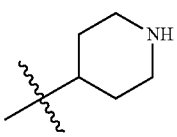 [SMILES: *C1CCNCC1] | 538.3 |
| 31 | i-PrSO₂ | C | 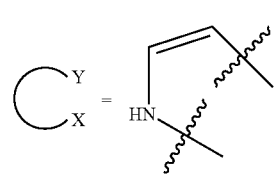 | / | CD₃ | Me | 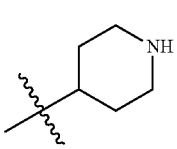 [SMILES: *C1CCNCC1] | 538.3 |

TABLE 9-continued

Structure of Compound I

| No. | R1: | A | X | Y | R$_2$ | R$_4$ | R$_3$ | LC-MS (M + 1) |
|---|---|---|---|---|---|---|---|---|
| 32 | i-PrSO$_2$ | C | (ring with S, X, Y) | / | CD$_3$ | Me | 4-piperidinyl (NH) | 555.3 |
| 33 | i-PrSO$_2$ | C | Cl | H | CD$_3$ | H | 4-(thiomorpholin-4-yl)piperidin-1-yl | 620.2 |
| 34 | i-PrSO$_2$ | C | Cl | H | CD$_3$ | H | 4-(4-aminopiperidin-1-yl)piperidin-1-yl | 617.3 |
| 35 | i-PrSO$_2$ | C | Cl | H | CD$_3$ | H | 4-morpholinopiperidin-1-yl | 604.3 |
| 36 | i-PrSO$_2$ | C | Cl | H | CD$_3$ | H | 4-(4-methylpiperazin-1-yl)piperidin-1-yl | 617.3 |
| 37 | Me$_2$P(O) | C | Cl | H | CD$_3$ | H | 4-(dimethylamino)piperidin-1-yl | 532.2 |
| 38 | Me$_2$P(O) | C | Cl | H | CD$_3$ | Me | 4-piperidinyl (NH) | 503.3 |
| 39 | i-PrSO$_2$ | N | / | H | CD$_3$ | H | 4-piperidinyl (NH) | 486.3 |
| 40 | i-PrSO$_2$ | N | / | H | CD$_3$ | Me | 4-piperidinyl (NH) | 500.3 |
| 41 | i-PrSO$_2$ | N | / | H | CD$_3$ | H | piperazin-1-yl (NH) | 487.3 |

TABLE 9-continued

Structure of Compound I

| No. | R1: | A | X | Y | R$_2$ | R$_4$ | R$_3$ | LC-MS (M + 1) |
|---|---|---|---|---|---|---|---|---|
| 42 | i-PrSO$_2$ | N | / | H | CD$_3$ | Me | (piperazine-piperidine) | 501.3 |
| 43 | i-PrSO$_2$ | N | / | H | CD$_3$ | H | (piperidine-piperazine-N-Me) | 484.3 |

II. Biological Activity Test

Anaplastic Lymphoma Kinase (ALK) Inhibitory Activity

The in-vitro kinase assay was performed using the HTRF kinEASE TK kit available from Cisbio. The operation steps are indicated in the instructions of the kit. This method was used to detect the inhibitory effect of the compound to be tested on the activity of ALK enzymes in vitro, including wild-type ALK (Cat.PV3867, Invitrogen), ALK L1196M (Cat. PV6168, Life technologies), and ALK F1174L (Cat. PV6160, Life technologies). The specific operation steps were as follows.

(1) First, a 2.5% DMSO solution was prepared with 1× kinase buffer previously formulated (where a too high concentration of DMSO had influence on the reaction, and the final concentration of DMSO was controlled to 1%), and then the compound to be tested was diluted with the 2.5% DMSO solution corresponding to the enzyme. The compound had a screening concentration of 100 nM, 10 nM and 1 nM. In addition to the control wells, 4 µL of the diluted compound solution to be tested was added to the reaction wells, and 4 µL of the 2.5% DMSO solution corresponding to the ALK enzyme previously formulated was added to the control wells.

(2) 2 µL of a TK-biotin substrate solution previously formulated in a substrate concentration corresponding to the ALK enzyme was added to all reaction wells.

(3) 2 µL of a previously prepared enzyme solution of corresponding concentration was added to all the reaction wells except the negative wells, and 2 µL of the 1× kinase buffer corresponding to the enzyme was added to the negative wells to make up the volume. The plate was sealed with a membrane, and incubated for 10 min at room temperature after mixing uniformly, such that the compounds were bond to the enzyme fully.

(4) 2 µL of an ATP solution in a concentration corresponding to the ALK enzyme was added to all the reaction wells to initiate the kinase reaction, where the enzyme reaction time by ALK was 60 minutes.

(5) An ALK test solution was prepared 5 minutes before the end of the kinase reaction. Streptavidin-XL665 and TK antibody europium cryptate (1:100) solutions for assay having a concentration corresponding to the enzyme were prepared using the detection buffer in the kit.

(6) After the completion of the kinase reaction, 5 µl of diluted Streptavidin-XL665 was added to all the reaction wells respectively, and mixed uniformly, and then the diluted TK antibody europium cryptate solution for assay was added immediately.

(7) The plate was sealed, mixed uniformly and allowed to react at room temperature for 1 h. The fluorescence signal (excitation at 320 nm, and emission at 665 nm and 615 nm) was detected using the ENVISION instrument (Perkinelmer). The inhibition rate for each well was calculated from the values of the fully active wells and the background signal wells. The values of replicated wells were averaged, and the half-maximal inhibitory activity (IC50) of each compound to be tested was fitted with a professional drawing analysis software PRISM 5.0.

The inhibitory activity of each compound against ALK enzyme obtained by the above method is as shown in Table 10.

TABLE 10

Inhibitory activity of each compound for ALK enzyme

| No. | R1: | A | X | Y | R$_2$ | R$_4$ | R$_3$ | IC$_{50}$ range |
|---|---|---|---|---|---|---|---|---|
| 1 | i-PrSO$_2$ | C | H | H | CD$_3$ | Me | (piperidine-NH) | +++ |
| 2 | i-PrSO$_2$ | C | F | H | CD$_3$ | Me | (piperidine-NH) | +++ |

TABLE 10-continued
Inhibitory activity of each compound for ALK enzyme
| No. | R1: | A | X | Y | $R_2$ | $R_4$ | $R_3$ | $IC_{50}$ range |
|---|---|---|---|---|---|---|---|---|
| 3 | i-PrSO$_2$ | C | Cl | H | CD$_3$ | Me | 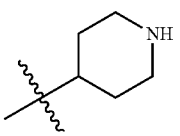 [SMILES: *C1CCNCC1] | +++ |
| 4 | i-PrSO$_2$ | C | Br | H | CD$_3$ | Me | 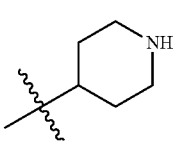 [SMILES: *C1CCNCC1] | +++ |
| 5 | i-PrSO$_2$ | C | CF$_3$ | H | CD$_3$ | Me | 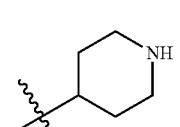 | +++ |
| 6 | i-PrSO$_2$ | C | CN | H | CD$_3$ | Me | 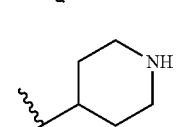 | +++ |
| 7 | i-PrSO$_2$ | C | OMe | H | CD$_3$ | Me | 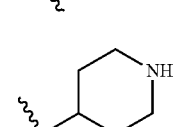 | +++ |
| 8 | i-PrSO$_2$ | C | Me | H | CD$_3$ | Me | 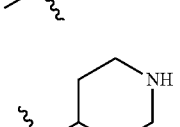 | +++ |
| 9 | i-PrSO$_2$ | C | Et | H | CD$_3$ | Me |  | +++ |
| 10 | i-PrSO$_2$ | C | NO$_2$ | H | CD$_3$ | Me | 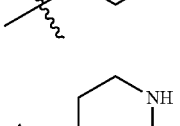 | +++ |
| 11 | i-PrSO$_2$ | C | Ph | H | CD$_3$ | Me | 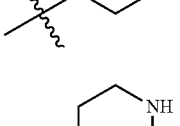 | ++ |
| 12 | i-PrSO$_2$ | C | 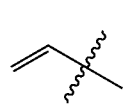 | H | CD$_3$ | Me | 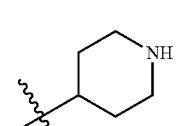 | +++ |

TABLE 10-continued

Inhibitory activity of each compound for ALK enzyme

| No. | R1: | A | X | Y | R₂ | R₄ | R₃ | IC₅₀ range |
|---|---|---|---|---|---|---|---|---|
| 13 | i-PrSO₂ | C | ethynyl | H | CD₃ | Me | 4-piperidinyl (NH) | +++ |
| 14 | i-PrSO₂ | C | Cl | H | CD₂CD₃ | Me | 4-piperidinyl (NH) | +++ |
| 15 | i-PrSO₂ | C | Cl | H | CD₃ | H | 4-piperidinyl (NH) | +++ |
| 16 | i-PrSO₂ | C | Cl | H | CD₃ | H | 4-piperazinyl (NH) | +++ |
| 17 | i-PrSO₂ | C | Cl | H | CD₃ | Me | 4-piperazinyl (NH) | +++ |
| 18 | i-PrSO₂ | C | Cl | H | CD₃ | Cl | 4-piperidinyl (NH) | +++ |
| 19 | i-PrSO₂ | C | Cl | H | CD₂CD₃ | Cl | 4-piperidinyl (NH) | +++ |
| 20 | i-PrSO₂ | C | Cl | H | CD₂CD₃ | H | 4-piperidinyl (NH) | +++ |
| 21 | i-PrSO₂ | C | Cl | H | CD₃ | F | 4-piperidinyl (NH) | +++ |
| 22 | i-PrSO₂ | C | Cl | H | CD₃ | CF₃ | 4-piperidinyl (NH) | +++ |

TABLE 10-continued

Inhibitory activity of each compound for ALK enzyme

| No. | R1: | A | X | Y | R₂ | R₄ | R₃ | IC₅₀ range |
|---|---|---|---|---|---|---|---|---|
| 23 | i-PrSO₂ | C | Cl | H | CD₃ | CN | 4-piperidinyl (NH) | +++ |
| 24 | i-PrSO₂ | C | pyrrole (NH) | / | CD₃ | H | 4-(4-methylpiperazin-1-yl)piperidin-1-yl | ++ |
| 25 | i-PrSO₂ | C | pyrrole (NH) | / | CD₃ | H | 4-(4-methylpiperazin-1-yl)piperidin-1-yl | ++ |
| 26 | i-PrSO₂ | C | thiophene | / | CD₃ | H | 4-(dimethylamino)piperidin-1-yl (NMe₂) | ++ |
| 27 | i-PrSO₂ | C | thiophene | / | CD₃ | H | 4-(dimethylamino)piperidin-1-yl (NMe₂) | ++ |
| 28 | i-PrSO₂ | C | phenyl | / | CD₃ | H | 4-morpholinopiperidin-1-yl | ++ |
| 29 | i-PrSO₂ | C | phenyl | / | CD₃ | Me | 4-piperidinyl (NH) | ++ |
| 30 | i-PrSO₂ | C | pyrrole (NH) | / | CD₃ | Me | 4-piperidinyl (NH) | ++ |

TABLE 10-continued

Inhibitory activity of each compound for ALK enzyme

| No. | R1: | A | X | Y | R$_2$ | R$_4$ | R$_3$ | IC$_{50}$ range |
|---|---|---|---|---|---|---|---|---|
| 31 | i-PrSO$_2$ | C | (X=HN, ring with Y) | / | CD$_3$ | Me | 4-piperidinyl (NH) | ++ |
| 32 | i-PrSO$_2$ | C | (X, Y = thiophene ring) | / | CD$_3$ | Me | 4-piperidinyl (NH) | ++ |
| 33 | i-PrSO$_2$ | C | Cl | H | CD$_3$ | H | 4-(thiomorpholin-4-yl)piperidin-1-yl | +++ |
| 34 | i-PrSO$_2$ | C | Cl | H | CD$_3$ | H | 4-amino-[1,4'-bipiperidin]-1'-yl | +++ |
| 35 | i-PrSO$_2$ | C | Cl | H | CD$_3$ | H | 4-(morpholin-4-yl)piperidin-1-yl | +++ |
| 36 | i-PrSO$_2$ | C | Cl | H | CD$_3$ | H | 4-(4-methylpiperazin-1-yl)piperidin-1-yl | +++ |
| 37 | Me$_2$P(O) | C | Cl | H | CD$_3$ | H | 4-(dimethylamino)piperidin-1-yl | +++ |
| 38 | Me$_2$P(O) | C | Cl | H | CD$_3$ | Me | 4-piperidinyl (NH) | +++ |
| 39 | i-PrSO$_2$ | N | / | H | CD$_3$ | H | 4-piperidinyl (NH) | +++ |
| 40 | i-PrSO$_2$ | N | / | H | CD$_3$ | Me | 4-piperidinyl (NH) | +++ |

TABLE 10-continued

Inhibitory activity of each compound for ALK enzyme

| No. | R1: | A | X | Y | $R_2$ | $R_4$ | $R_3$ | $IC_{50}$ range |
|---|---|---|---|---|---|---|---|---|
| 41 | i-PrSO$_2$ | N | / | H | CD$_3$ | H | piperazinyl-NH | +++ |
| 42 | i-PrSO$_2$ | N | / | H | CD$_3$ | Me | piperazinyl-NH | +++ |
| 43 | i-PrSO$_2$ | N | / | H | CD$_3$ | H | piperidinyl-piperazinyl-N | +++ |
| 44 | i-PrSO$_2$ | C | Cl | H | CD(CD$_3$)$_2$ | Me | piperidinyl-NH | ++ |
| 45 | i-PrSO$_2$ | C | Cl | H | Me | Me | piperidinyl-NH | ++ |

$IC_{50}$ range: +++ represents 1-10 nM; ++ represents 10-100 nM; and + represents 100-1 uM.

Growth Inhibition Test of the Series of Compounds on Various Tumor Cells (CCK8 Detection)

1. Cell lines:
   (1) Ba/F3 mouse IL-3 dependent pro-B lymphocyte cell line, RPMI 1640+10% FBS+10 ng/ml Interleukin-3+1% Sodium Pyruvate;
   (2) Karpas 299 human T lymphoma cell line, RPMI 1640+10% FBS+1% Sodium Pyruvate;
   (3) NCI-H2228 human non-small cell lung cancer cell line, RPMI 1640+10% FBS+1% Sodium Pyruvate;
   (4) NCI-H3122 human lung cancer cell line, RPMI 1640+10% FBS+1% Sodium Pyruvate.
2. Reagents and materials:
   CCK8 kit; anti-tumor compounds; DMSO
3. Test method:
   (1) Cell culture
   a) Cells in logarithmic growth phase were collected, counted, and re-suspended in a complete medium.
   b) The cell concentration was adjusted to an appropriate concentration, and inoculated into a 96-well plate in an amount of 100 μl of cell suspension per well.
   c) The cells were incubated for 24 hrs in an incubator at 37° C. with 100% relative humidity and 5% CO$_2$.
   (2) Test of relative inhibition rate
   1) Cells in logarithmic growth phase were collected, counted, and re-suspended in a complete medium. The cell concentration was adjusted to an appropriate concentration (determined according to the optimal test result of cell density), and inoculated into a 96-well plate in an amount of 100 μl of cell suspension per well. The cells were incubated for 24 hrs in an incubator at 37° C. with 100% relative humidity and 5% CO$_2$.
   2) The compound to be tested was diluted with the medium to the corresponding action concentration, and the cells were added in an amount of 25 l/well. The final concentration of the compound was from 10 μM to 0 μM, and a total of 10 concentration points were given by dilution over a 4-fold gradient.
   3) The cells were incubated for 72 hrs in an incubator at 37° C. with 100% relative humidity and 5% CO$_2$.
   4) The medium was aspirated off, a complete medium containing 10% CCK-8 was added and the cells were incubated in an incubator at 37° C. for 2-4 hrs.
   5) The absorbance at 450 nm was measured on the SpectraMax M5 Microplate Reader after gentle shaking, and the absorbance at 650 nm was used as a reference to calculate the inhibition rate.
4. Data processing and results The inhibition rate of the drug on tumor cell growth was calculated by a formula below: Tumor cell growth inhibition %=[($A_c$-$A_s$)/($A_c$-$A_b$)]×100%

$A_s$: OA of the sample (cells+CCK-8+compound to be tested)

$A_c$: OA of the negative control (cells+CCK-8+DMSO)

$A_b$: OA of the positive control (medium+CCK-8+DMSO)

The IC$_{50}$ curve was fitted using the software Graphpad Prism 5 and using the calculation formula log(inhibitor) vs response and the IC$_{50}$ value was calculated. The inhibitory activities (IC$_{50}$) of various compounds for the growth of various tumor cells are shown in Table 11.

TABLE 11

Inhibitory activities (IC$_{50}$) of various compounds against the growth of various tumor cells

| Compound | Ba/F3 cells | Karpas 299 cells | NCI-H2228 cells | NCI-H3122 cells |
|---|---|---|---|---|
| I-3: | 1242 | 7.643 | 41.3 | 4.031 |
| I-14: | 1993 | 5.23 | 45.5 | 6.09 |
| [structure of compound] | 2891 | 45.68 | 111.3 | 28.41 |
| Ceritinib | 2387 | 35.57 | 97.06 | 27.2 |

In-Vivo Pharmacodynamic Evaluation

SCID Beige mice, female, 5-6 weeks old, weighed 18+2 g, purchased from Beijing HFK Bioscience Co., Ltd., bred in an SPF level environment.

NCI-H2228 cells were cultured in PRMI-1640 containing 10% fetal bovine serum (FBS) and 1% sodium pyruvate. The cells were cultured in an incubator at 37° C. with 5% CO$_2$.

Establishment of subcutaneous tumor transplantation model in nude mice by cell inoculation: Tumor cells in logarithmic growth phase were collected, counted and re-suspended in PRMI-1640 basal medium. Matrigel was added at a ratio of 1:1, and the concentration of the cell suspension was adjusted to 6×10$^7$/ml. Tumor cells were subcutaneously inoculated to the right back of nude mice in an amount of 6×10$^6$/0.1 mL/mouse using a 1 mL syringe (with a 4 gauge needle).

When the tumor volume reached about 200 mm$^3$, the animals were randomly grouped according to randomized block method, so that the difference in tumor volume of each group was within 10% of the mean. There were 5 groups in total, each having 8 animals. The day of grouping was recorded as Day 0, and the animals were administered immediately after grouping. Compound I-3 of the present invention and Ceritinib were orally administered once a day for consecutive 14 days, and then observed for 7 days. The weight and tumor size of the animals were measured twice a week during the experiment. The clinical symptoms were observed and recorded daily. After the animals were weighed for the last time on Day 21, they were sacrificed by euthanization with CO$_2$. The tumors were taken, weighed and photographed, and the average tumor size was calculated, to investigate the growth inhibitory effect of the test substance Compound I-3 on human lung cancer NCI-H2228 nude mice xenografts under the experimental conditions.

When the tumor in the tumor-bearing mice grew to a measurable size, the mice were randomly divided into 5 groups according to the principle of equal mean tumor volume using SPSS 17.0 software. Compound I-3 was administered by intragastric administration at a dosage of 30, 10, and 3 mg/kg per day. The positive control ceritinib was administered by intragastric administration at a dose of 10 mg/kg per day in a volume of 0.1 ml/10 g. These agents were administered once a day for consecutive 14 days. The animals in the negative control group were given an equal amount of solvent (1% DMSO in physiological saline). During the administration and recovery periods, the body weight and tumor size of the mice were measured 2-3 times per week. The tumor volume and relative tumor volume were calculated based on the measured data. The tumor volume (TV) was calculated by a formula below: TV=1/2× a×b$^2$, where a and b represent the major and minor diameters of the tumor, respectively. According to the measurement results, the relative tumor volume (RTV) was calculated, by a formula below: RTV=V$_t$/V$_0$, where V$_0$ is the tumor volume at the start of the experiment, and V$_t$ is the tumor volume measured each time. The evaluation indices for the anti-tumor activity were the relative tumor growth rate T/C (%), which was calculated by a formula below: T/C (%)=T$_{RTV}$/C$_{RTV}$×100%, where T$_{RTV}$ is the RTV of the treatment group and C$_{RTV}$ is the RTV of the negative control group; and the relative tumor growth inhibition rate (tumor inhibition rate) (%)=(1−T/C)×100%. The results are shown in Table 12.

TABLE 12

Therapeutic effect of the compound of the present invention on NCI-H2228 nude mice xenografts

| Group | Dose (mg/kg) | Administration mode | RTV d$_{21}$ | IR (%) | T/C (%) |
|---|---|---|---|---|---|
| Blank group | 0 | qd | 3.75 ± 0.27 | — | — |
| I-3: | 3 | qd | 3.12 ± 0.23 | 12.86 | 77.45 |
| I-3: | 10 | qd | 1.70 ± 0.20*** | 53.39 | 45.33 |
| I-3: | 30 | qd | 0.79 ± 0.17*** | 77.14 | 21.07 |
| Ceritinib | 10 | qd | 2.68 ± 0.28* | 26.07 | 71.47 |

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A diphenylaminopyrimidine and triazine compound of Formula I, or a pharmaceutically acceptable salt, stereoisomer, hydrate or solvate thereof:

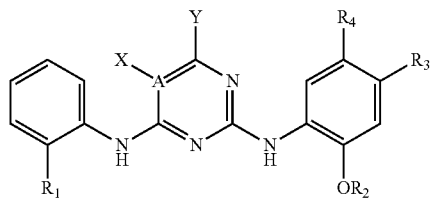

I wherein:

A is C;

X and Y are independently selected from the group consisting of hydrogen, halo, cyano, trifluoromethyl, alkoxy, alkyl, aryl, alkenyl, alkynyl, and nitro; or X and Y, together with the atoms to which they are attached, form a phenyl ring or an heteroaromatic ring, the heteroaromatic ring containing one or more of oxygen, sulfur and nitrogen heteroatoms;

$R_1$ is

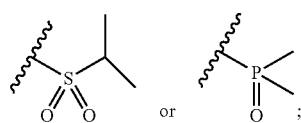

$R_2$ is $CD_3$ or $CD_2CD_3$;

$R_3$ is selected from

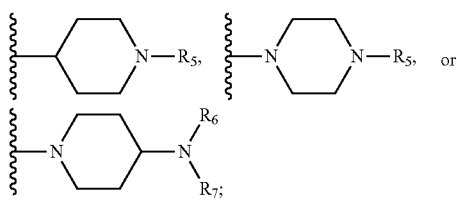

$R_4$ is selected from the group consisting of hydrogen, methyl, trifluoromethyl, cyano and halo;

$R_5$ is selected from the group consisting of hydrogen, alkyl, substituted and unsubstituted phenyl, allyl and propargyl; and $R_6$ and $R_7$ are independently selected from the group consisting of hydrogen, alkyl, substituted and unsubstituted phenyl, allyl and propargyl; or $R_6$ and $R_7$, together with the N atom to which they are attached, form a substituted or unsubstituted heterocycloalkyl group, the heterocycloalkyl group containing one or more of oxygen, sulfur, nitrogen, sulfoxide and sulfone groups.

2. The diphenylaminopyrimidine and triazine compound as claimed in claim 1, or a pharmaceutically acceptable salt, stereoisomer, hydrate or solvate thereof, wherein $R_1$ is

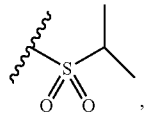 [SMILES: *S(=O)(=O)C(C)C]

$R_2$ is $CD_3$, X is halo, and Y is hydrogen.

3. The diphenylaminopyrimidine and triazine compound as claimed in claim 1, or a pharmaceutically acceptable salt, stereoisomer, hydrate or solvate thereof, wherein the diphenylaminopyrimidine and triazine compound is selected from the group consisting of:

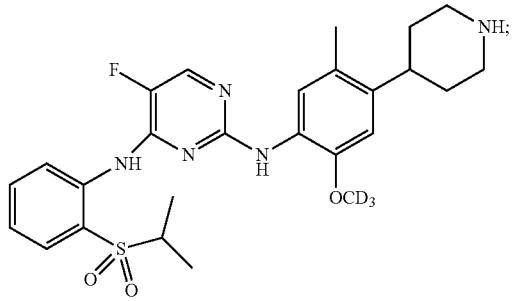

I-1

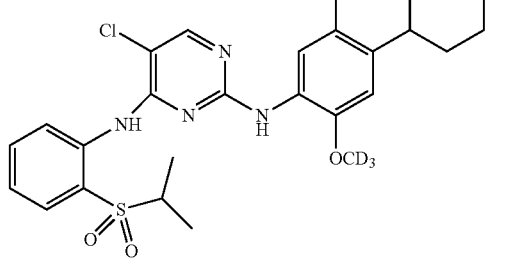

I-2

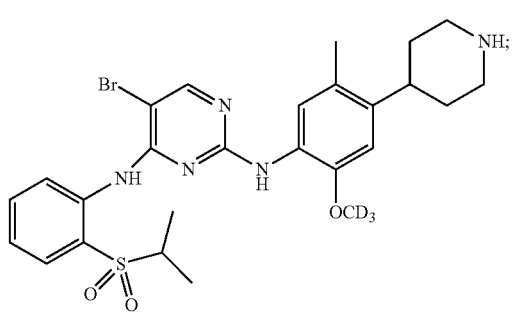

I-3

I-4

-continued
I-5
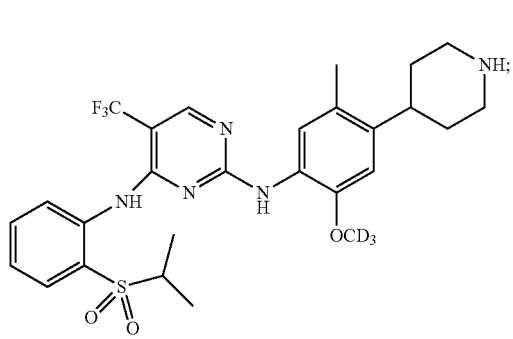
I-6
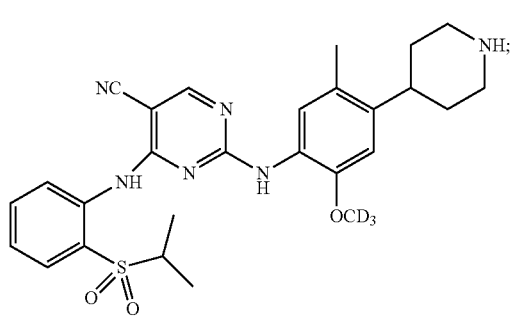
I-7
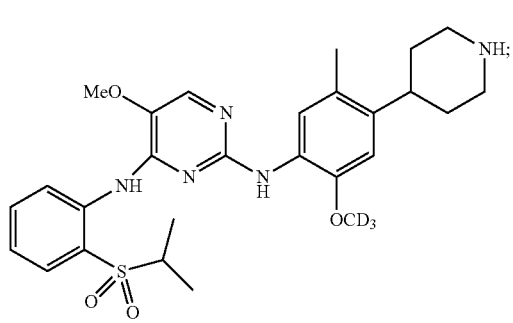
I-8
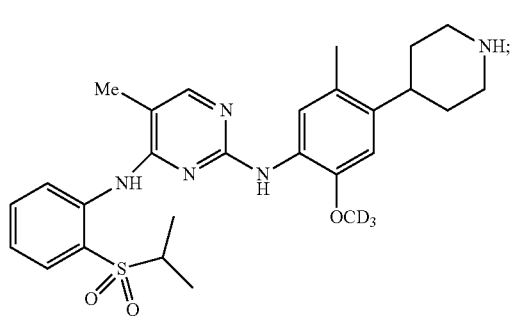
I-9
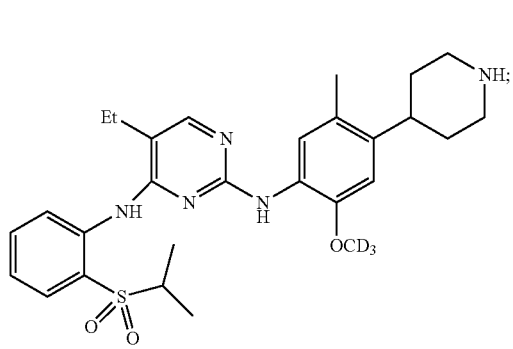
-continued
I-10
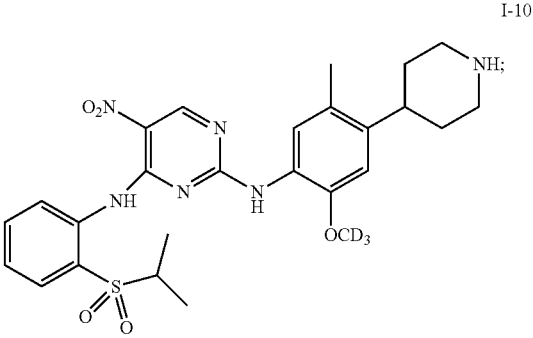
I-11
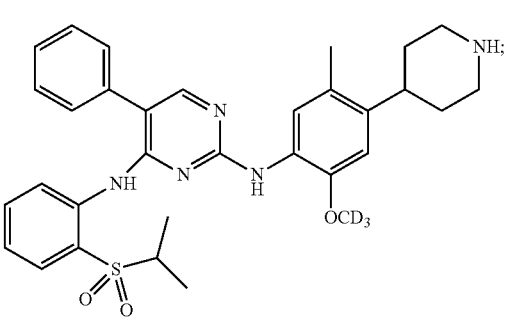
I-12
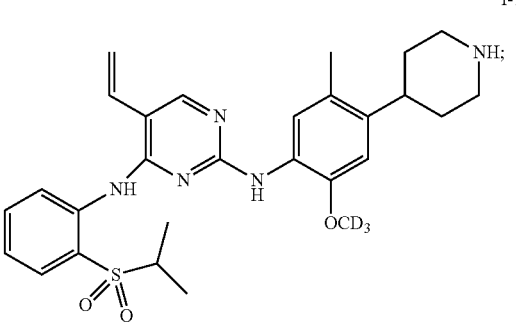
I-13
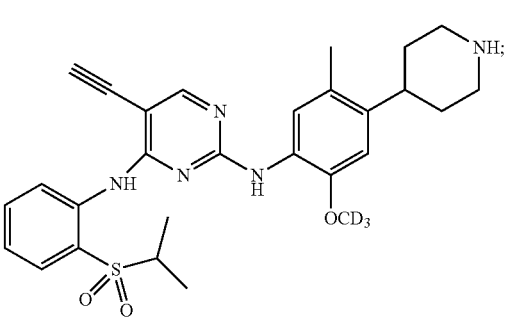
I-14
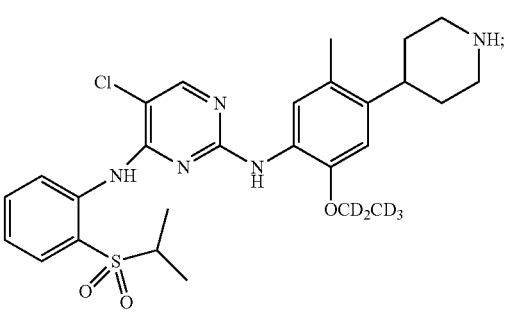

I-15
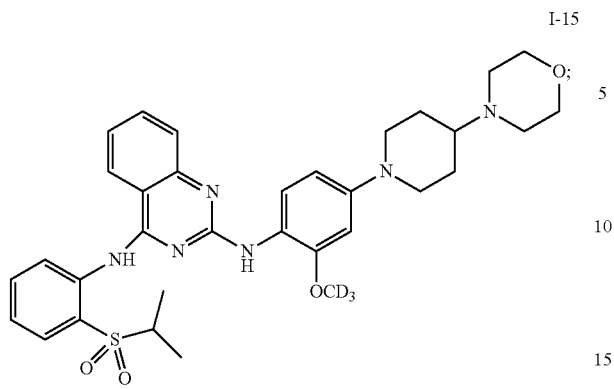
I-19
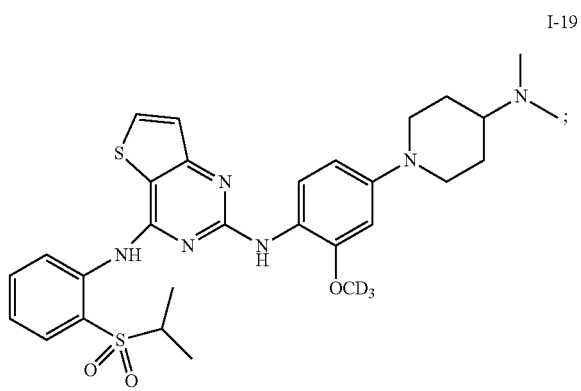
I-16
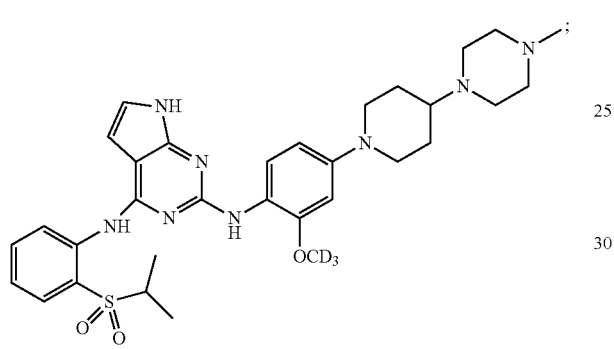
I-20
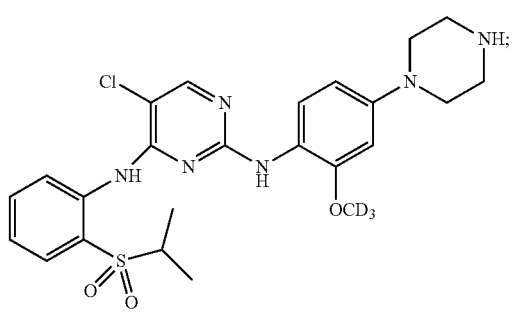
I-17
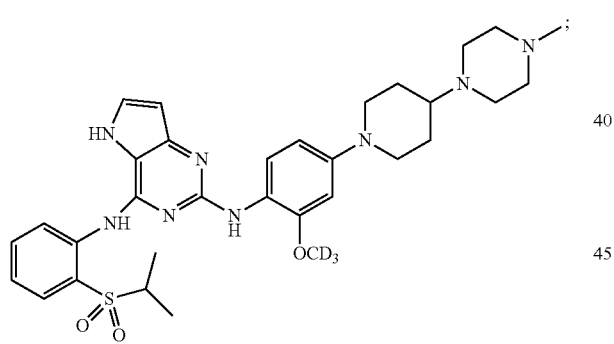
I-21
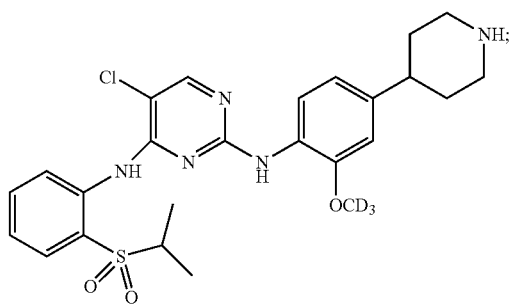
I-18
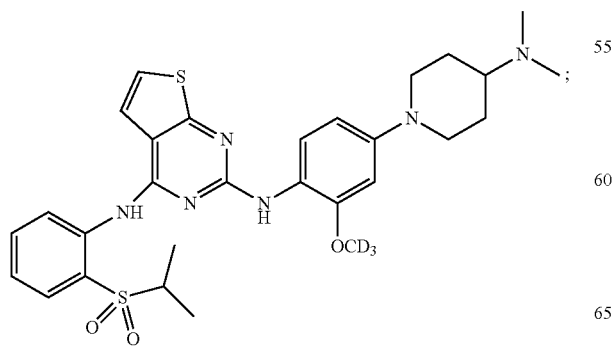
I-22
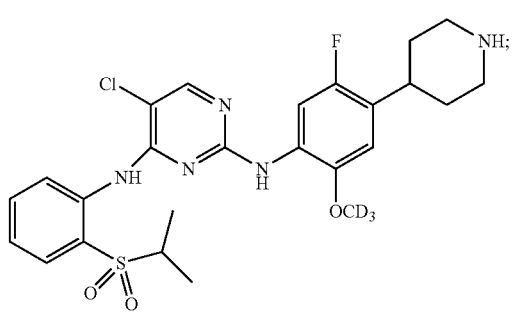

-continued
I-23
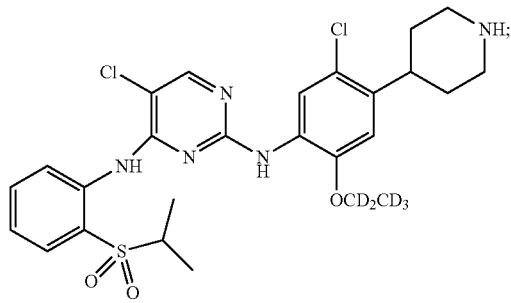
I-24
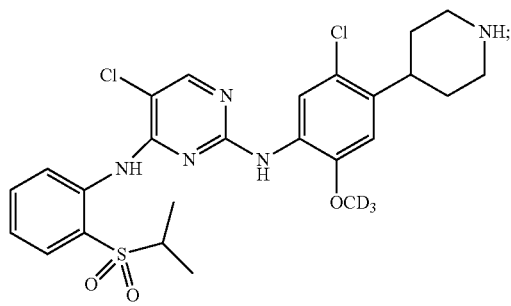
I-25
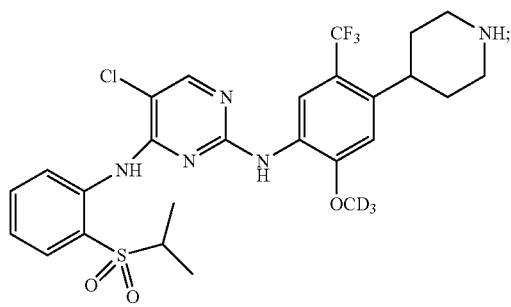
I-26
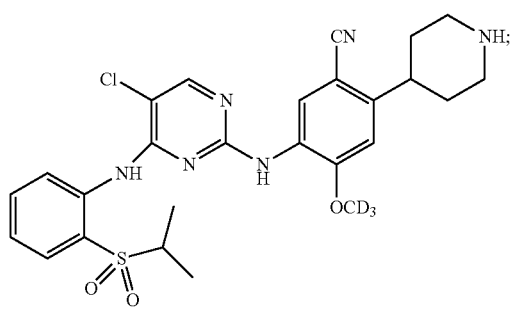
I-30
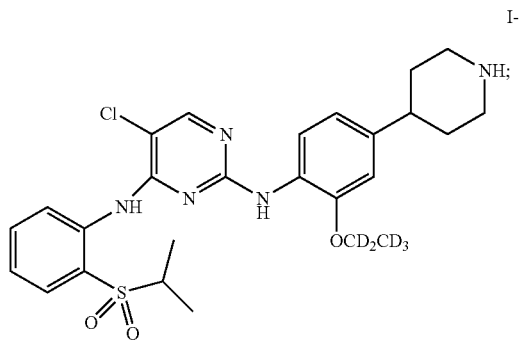
-continued
I-31
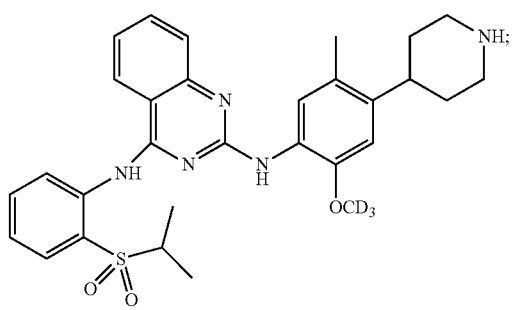
I-32
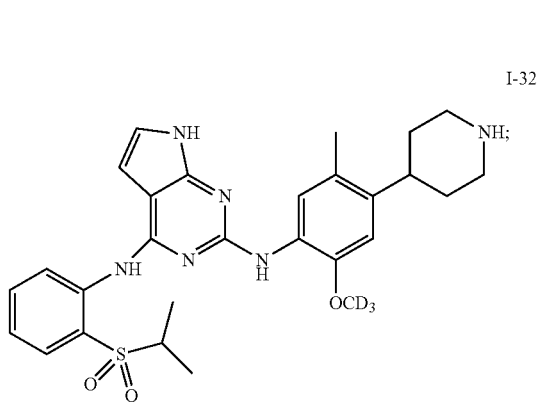
I-33
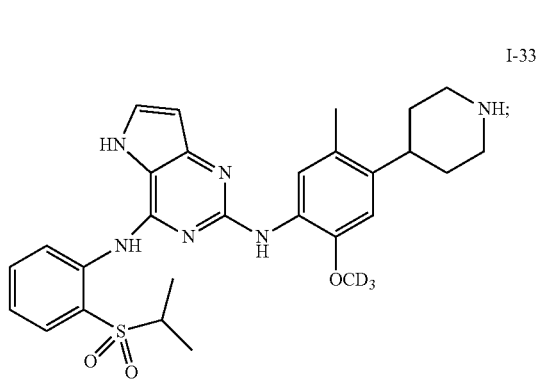
I-34
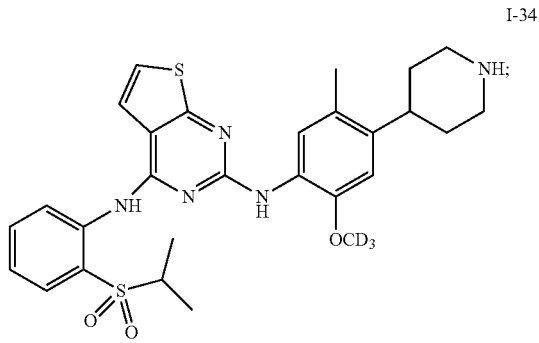

I-35
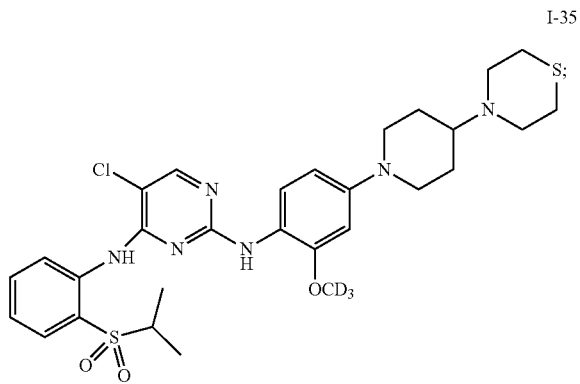

I-36
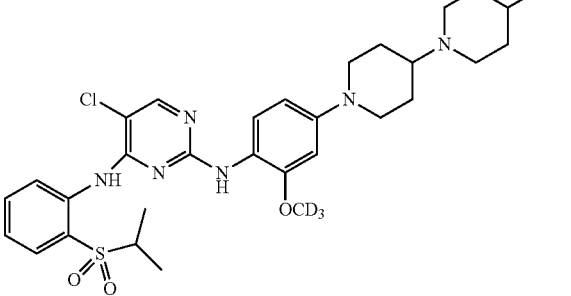

I-37
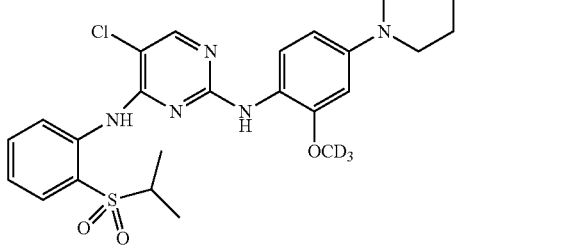

I-39
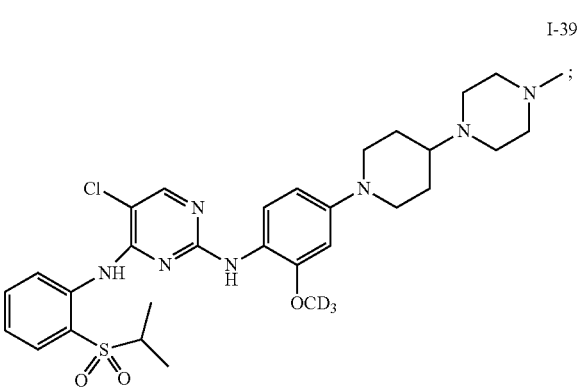

I-40
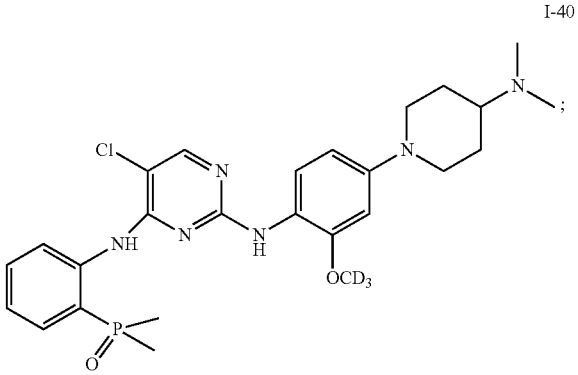

I-41
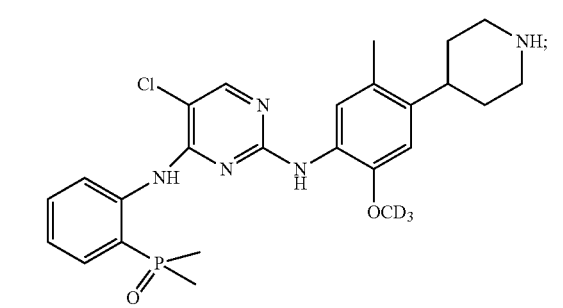

and

I-43
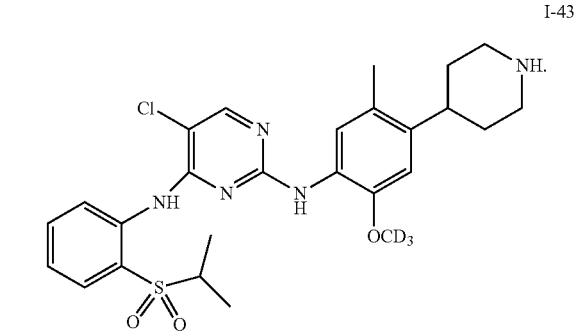

4. A pharmaceutical composition, comprising a diphenylaminopyrimidine and triazine compound, or a pharmaceutically acceptable salt, stereoisomer, hydrate or solvate thereof as claimed in claim 1, and a pharmaceutically acceptable carrier or excipient.

5. A method of treating a disease or disorder that benefits from inhibition of the ALK tyrosine kinase activity comprising:
treating a subject in need thereof with an ALK tyrosine kinase inhibitor,
wherein the ALK tyrosine kinase inhibitor is the diphenylaminopyrimidine and triazine compound of Formula I, or a pharmaceutically acceptable salt, stereoisomer, hydrate or solvate thereof as claimed in claim 1.

6. The method as claimed in claim 5, wherein the disease or disorder is selected from the group consisting of cancers, cell proliferative diseases, immune diseases or inflammation, infection, organ transplantation, viral diseases, cardiovascular diseases, and metabolic diseases.

7. The method as claimed in claim 6, wherein the cancers are selected from the group consisting of non-small cell lung cancer, neuroblastoma, melanoma leukemia and lymphoma.

8. The method as claimed in claim 6, wherein the immune diseases or inflammation are selected from the group consisting of rheumatoid arthritis, osteoarthritis, rheumatoid spondylitis, gout, asthma, bronchitis, rhinitis, chronic obstructive pulmonary disease and cystic fibrosis.

9. The method as claimed in claim 5, wherein the ALK tyrosine kinase inhibitor is administered alone or in combination with other therapeutic agents.

10. The method as claimed in claim 5, wherein the ALK tyrosine kinase inhibitor is administered orally, parenterally, transpulmonarily, intravenously or transdermally.

* * * * *